US012735432B2

(12) United States Patent
Xie et al.

(10) Patent No.: US 12,735,432 B2
(45) Date of Patent: Sep. 15, 2026

(54) PARP INHIBITOR CONTAINING PIPERAZINE STRUCTURE. PREPARATION METHOD THEREFOR AND PHARMACEUTICAL USE THEREOF

(71) Applicant: WIGEN BIOMEDICINE TECHNOLOGY (SHANGHAI) CO., LTD., Shanghai (CN)

(72) Inventors: Yuli Xie, Shanghai (CN); Yongcong Lv, Shanghai (CN); Lihui Qian, Shanghai (CN); Houxing Fan, Shanghai (CN)

(73) Assignee: WIGEN BIOMEDICINE TECHNOLOGY (SHANGHAI) CO., LTD., Shanghai (CN)

( * ) Notice: Subject to any disclaimer, the term of this patent is extended or adjusted under 35 U.S.C. 154(b) by 384 days.

(21) Appl. No.: 18/281,855

(22) PCT Filed: Apr. 19, 2022

(86) PCT No.: PCT/CN2022/087652
§ 371 (c)(1),
(2) Date: Sep. 13, 2023

(87) PCT Pub. No.: WO2022/222921
PCT Pub. Date: Oct. 27, 2022

(65) Prior Publication Data

US 2024/0336624 A1 Oct. 10, 2024

(30) Foreign Application Priority Data

Apr. 22, 2021 (CN) ......................... 202110439238.4

(51) Int. Cl.
*C07D 498/04* (2006.01)
*A61K 31/496* (2006.01)
(Continued)

(52) U.S. Cl.
CPC .......... *C07D 498/04* (2013.01); *A61K 31/496* (2013.01); *A61K 31/497* (2013.01);
(Continued)

(58) Field of Classification Search
CPC .. C07D 498/04; C07D 401/14; C07D 471/04; C07D 401/12; A61K 31/496;
(Continued)

(56) References Cited

FOREIGN PATENT DOCUMENTS

CN 102341394 A 2/2012
CN 107849040 A 3/2018
(Continued)

OTHER PUBLICATIONS

CAS Registry No. 184691-50-7, entered on Jan. 2, 1997. (Year: 1997).*
(Continued)

*Primary Examiner* — Matthew P Coughlin
*Assistant Examiner* — Ashli A Chicks
(74) *Attorney, Agent, or Firm* — SZDC Law PC

(57) ABSTRACT

Disclosed in the present invention are a PARP inhibitor containing a piperazine structure, a preparation method therefor and pharmaceutical use thereof. Particularly, the present invention relates to novel compounds of general formulas (1), (2), (3), (4) and (5) and/or a pharmaceutically acceptable salt thereof, a composition comprising the compounds of general formulas (1), (2), (3), (4) and (5) and/or the pharmaceutically acceptable salt thereof, a preparation method therefor and use thereof as a PARP inhibitor in the preparation of anti-tumor drugs.

(1)

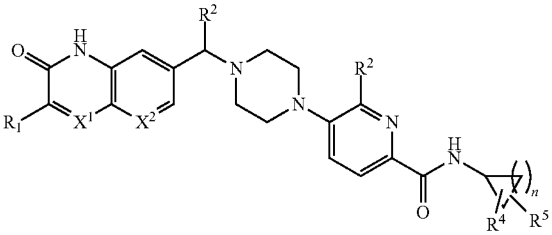

(2)

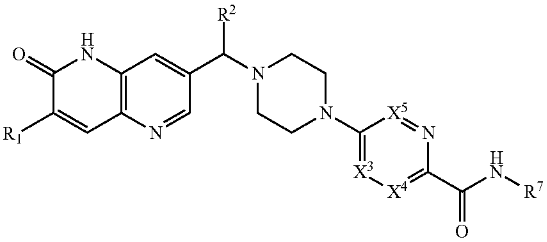

(3)

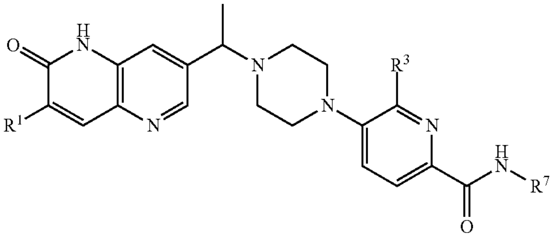

(4)

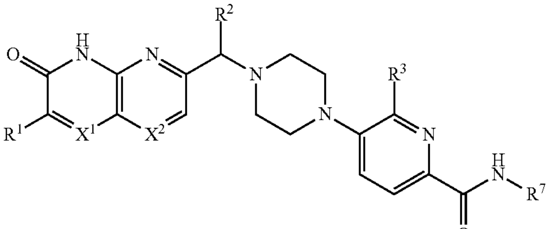

(Continued)

-continued (5)

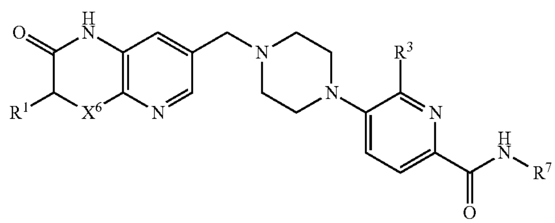

6 Claims, No Drawings

(51) Int. Cl.

| | |
|---|---|
| ***A61K 31/497*** | (2006.01) |
| ***A61K 31/498*** | (2006.01) |
| ***A61K 31/4985*** | (2006.01) |
| ***A61K 31/501*** | (2006.01) |
| ***A61K 31/506*** | (2006.01) |
| ***A61K 31/5383*** | (2006.01) |
| ***C07D 401/14*** | (2006.01) |
| ***C07D 471/04*** | (2006.01) |

(52) U.S. Cl.
CPC ........ *A61K 31/498* (2013.01); *A61K 31/4985* (2013.01); *A61K 31/501* (2013.01); *A61K 31/506* (2013.01); *A61K 31/5383* (2013.01); *C07D 401/14* (2013.01); *C07D 471/04* (2013.01)

(58) Field of Classification Search
CPC ................ A61K 31/497; A61K 31/498; A61K 31/4985; A61K 31/501; A61K 31/506; A61K 31/5383; A61P 35/00
See application file for complete search history.

(56) References Cited

FOREIGN PATENT DOCUMENTS

| | | | | | |
|---|---|---|---|---|---|
| CN | 117177972 | A | | 12/2023 | |
| EA | 033613 | B1 | | 11/2019 | |
| JP | 2011500758 | A | | 1/2011 | |
| JP | 2012515786 | A | | 7/2012 | |
| JP | 2012522007 | A | | 9/2012 | |
| JP | 2018521033 | A | | 8/2018 | |
| JP | 2020512298 | A | | 4/2020 | |
| WO | 2009053373 | A1 | | 4/2009 | |
| WO | 2010111626 | A2 | | 9/2010 | |
| WO | 2021013735 | A1 | | 1/2021 | |
| WO | WO-2022222966 | A1 | * | 10/2022 | ......... C07D 215/227 |
| WO | WO-2022222995 | A1 | * | 10/2022 | .............. A61P 35/00 |
| WO | WO-2022225934 | A1 | * | 10/2022 | ........... C07D 498/08 |

OTHER PUBLICATIONS

CAS Registry No. 33222-34-3, entered Registry Nov. 16, 1984. (Year: 1984).*

CAS Registry No. 104416-63-9, entered Registry Sep. 27, 1986. (Year: 1986).*

Dörwald, F. Zaragoza. Side Reactions in Organic Synthesis: A Guide to Successful Synthesis Design, Weinheim: WILEY-VCH Verlg GmbH & Co. KGaA, 2005, Preface. (Year: 2005).*

Jeffrey W. Johannes et al., Discovery of 5-{4-[(7-Ethyl-6-oxo-5,6-dihydro-1,5-naphthyridin-3-yl)methyl]piperazin-1-yl}-N-methylpyridine-2-carboxamide (AZD5305): A PARP1-DNA Trapper with High Selectivity for PARP1 over PARP2 and Other PARPs, Journal of Medicinal Chemistry, Sep. 27, 2021, vol. 64, No. 19, p. 14498-14512, DOI: 10.1021/acs.jmedchem.1c01012 (Sep. 27, 2021).

* cited by examiner

PARP INHIBITOR CONTAINING PIPERAZINE STRUCTURE. PREPARATION METHOD THEREFOR AND PHARMACEUTICAL USE THEREOF

The present application is the National Stage Application of PCT/CN2022/087652, filed on Apr. 19, 2022, which claims priority to Chinese Application CN 202110439238.4 filed on Apr. 22, 2021, which is incorporated herein by reference in its entirety.

TECHNICAL FIELD

The present invention relates to the field of pharmaceutical chemistry, and particularly to a novel compound having an inhibitory effect on poly (ADP-ribose) polymerase (PARP), a preparation method therefor and use of such compounds in preparing anti-tumor drugs.

BACKGROUND

Poly (ADP-ribose) polymerase (PARP) is expressed in most eukaryotic cells, and takes nicotinamide adenine dinucleotide (NAD+) as a substrate to catalyze the formation of ADP-ribose units or polymers thereof (PARs) on itself or other specific amino acid residues of proteins, so as to modify the PARs of the proteins and further regulate the degradation and functions of the proteins. The PARP family consists of 7 isoenzymes, including PARP-1, PARP-2, PARP-3, PARP-4 (Vault-PARP), tankyrases such as PARP-5 (TANK-1, TANK-2 and TANK-3), PARP-7 and PARP-10 [de la Lastra C A. et al., *Curr Pharm Des.,* 13(9), 933-962, 2007]. Although the PARP family is diverse in enzymes, PARP-1 is responsible for more than 90% of ADP-ribosylation (PAR) within cells. PARPs play important roles in events including chromosome structure regulation, gene transcription, DNA replication and recombination, and DNA repair. Among them, PARP-1 promotes ADP-ribosylation and polymerization, initiates DNA repair and regulates the recruitment and level of DNA repair proteins during DNA repair.

When DNA of tumor cells is damaged by chemotherapy drugs or ionizing radiation, etc., PARP-1 is quickly activated, the NAD+ is taken as the substrate, and a large amount of PARs are synthesized at a DNA damage part to modify histones. DNA repair proteins are then recruited to initiate DNA repair. PARP-1 is mainly involved in the repair of single strand DNA breaks (SSBs). When PARP-1 is inhibited by a PARP inhibitor, SSBs cannot be repaired, and during S-phase DNA replication, the SSBs are converted into double strand breaks (DSBs), thereby inhibiting the function of PARP-1 and leading to accumulation of DSBs in the cells. Repair of the DSBs by the body is mainly achieved in two manners: homologous recombination (HR) and non-homologous DNA end joining (NHEJ), wherein repair by homologous recombination is a main manner of S-phase DSB repair, and the repair reliability is high. BRCA1 and BRCA2 play an important role in repair by the homologous recombination. The BRCA1 and BRAC2 deficiency results in limited DSB repair. The research shows that BRCA1/2 mutation is found in ovarian cancer, breast cancer and prostate cancer, and the cancer cells with BRCA1 and BRCA2 deficiency are particularly sensitive to the PARP inhibitor. This may result from inhibition of PARP-1 by the PAPR inhibitor, the DSBs are induced, and due to BRCA1/2 deficiency, repair is inhibited, thereby inducing cell death. Therefore, the PARP inhibitor has a good effect on clinical treatment of tumors with BRCA1/2 deficiency. The PARP inhibitor can be used alone or in combination with chemotherapy drugs and radiotherapy drugs, thereby achieving the purposes of reducing dosage and improving efficacy. Olaparib is the first PARP inhibitor approved for marketing. With the expanding indications of the PARP inhibitor, the PARP inhibitor is also used extensively, not only around tumors, but also has certain effects on stroke, myocardial ischemia, inflammation and diabetes.

Although efforts to develop the PARP inhibitor for the treatment of cancer and other diseases are ongoing, such inhibitors lack certain specificity for PAPR-family proteins, have non-negligible toxic and side effects, and are prone to drug resistance. Therefore, the development of specific and highly active PARP-1 inhibitors is of important clinical value.

SUMMARY

The present invention provides a compound of general formula (1), or an isomer, a crystalline form, a pharmaceutically acceptable salt, a hydrate, or a solvate thereof:

(1)

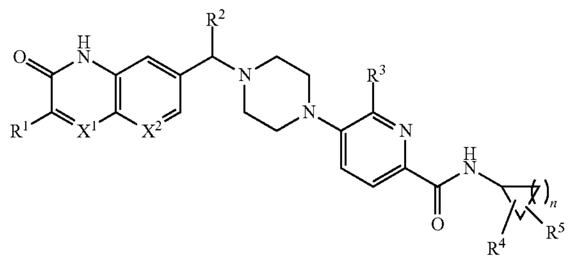

wherein in general formula (1):

$R^1$ is (C1-C4) alkyl, (C1-C4) fluoroalkyl, or (C3-C5) cycloalkyl;

$R^2$ is H or (C1-C3) alkyl;

$R^3$ is H, F, Cl, (C1-C4) alkyl, or (C1-C4) fluoroalkyl;

n is 1 or 2;

$R^4$ and $R^5$ represent two substituents on a cycloalkyl ring, and are each independently H or F; and $X^1$ and $X^2$ are each independently CH or N.

In another specific embodiment of the present invention, the compound of general formula (1) has one of the following structures:

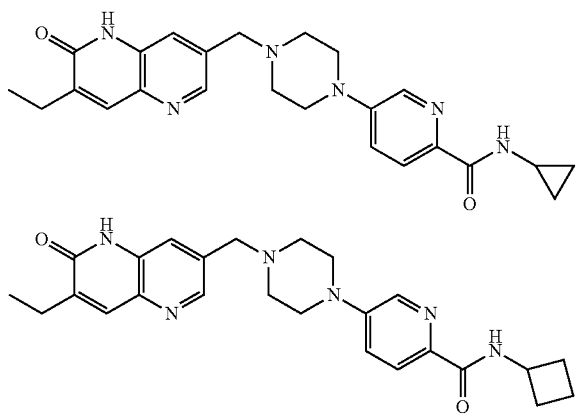

-continued
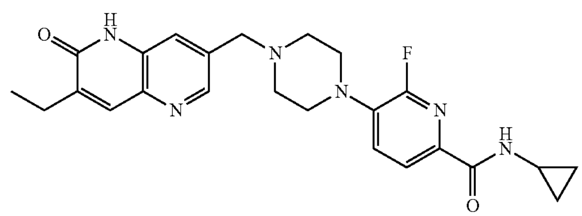
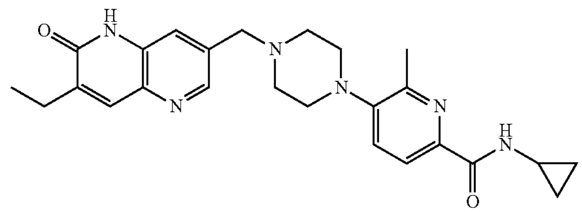
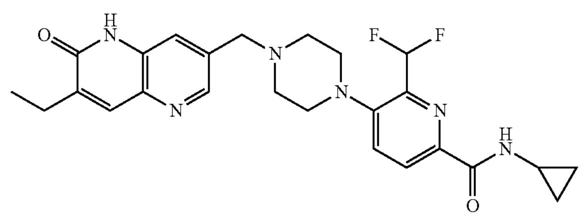
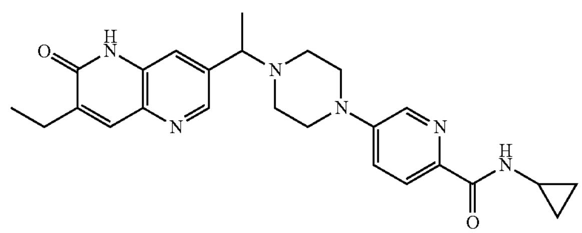
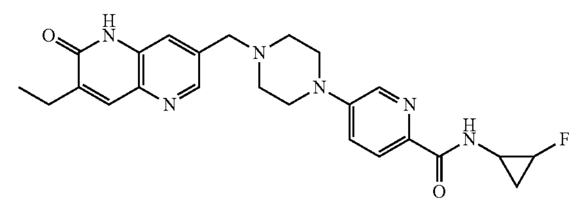
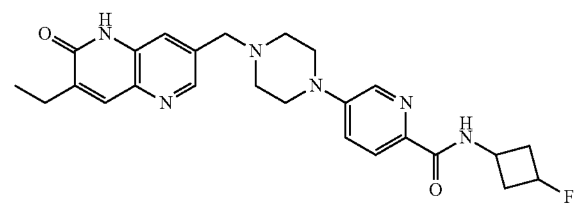
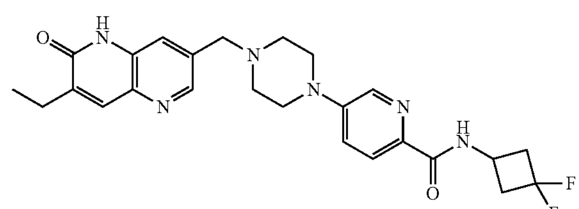
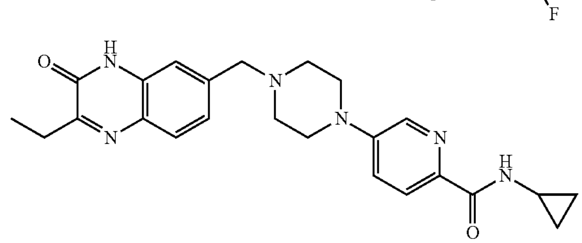
-continued
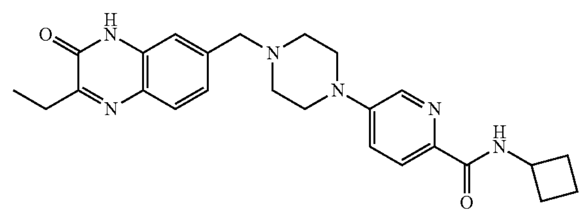
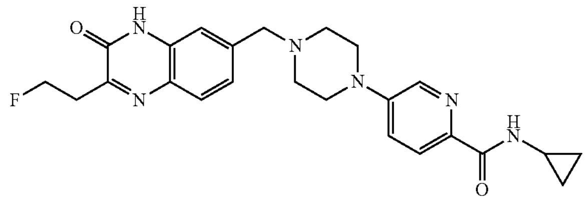
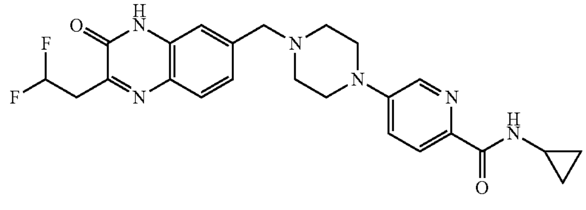
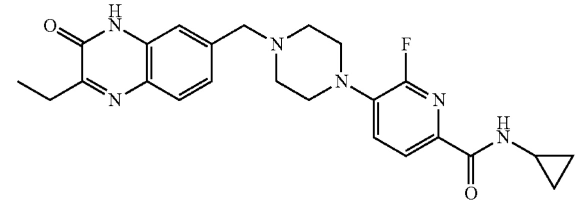
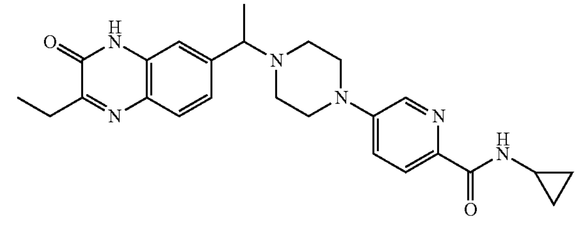
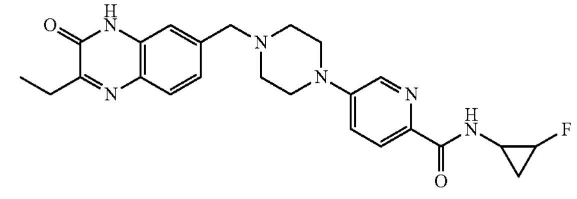
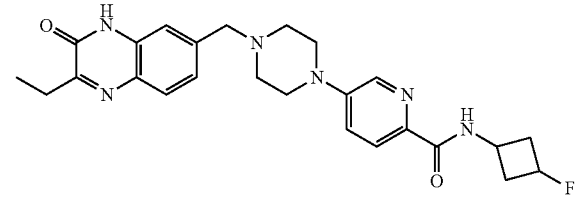
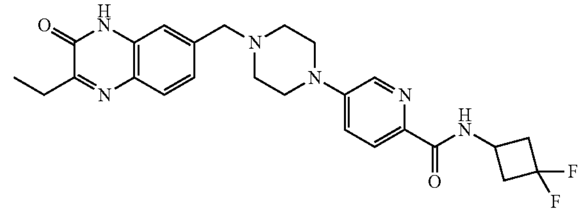

-continued

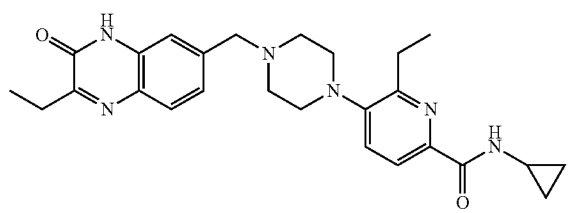

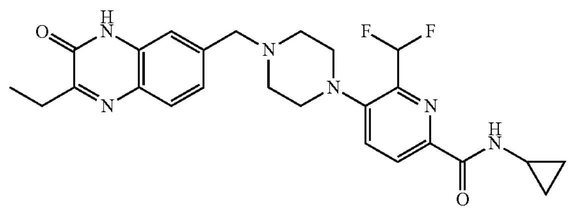

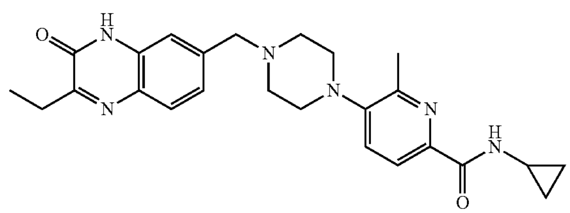

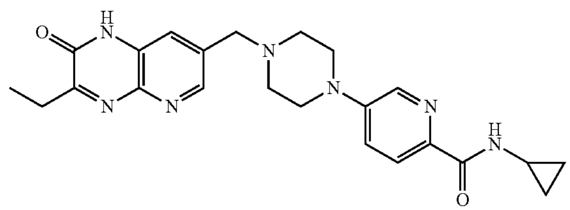

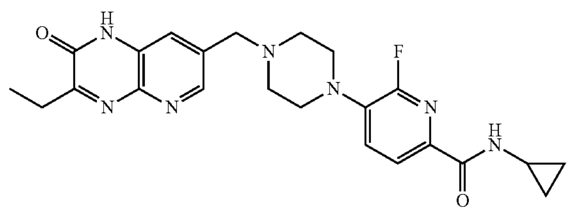

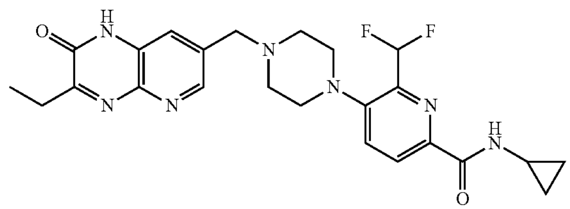

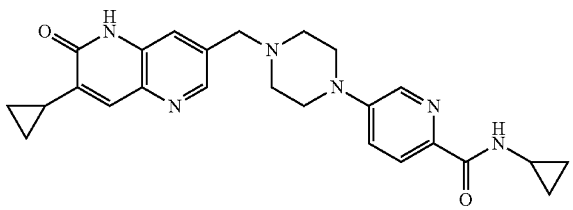

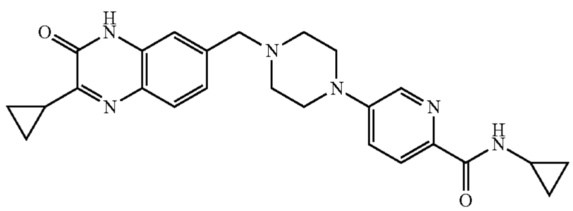

-continued

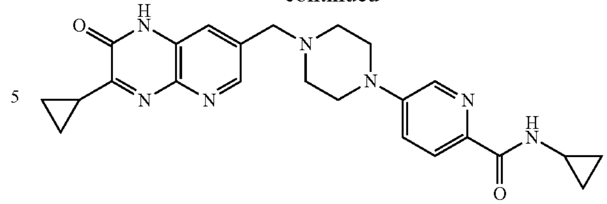

The present invention provides a compound of general formula (2), or an isomer, a crystalline form, a pharmaceutically acceptable salt, a hydrate, or a solvate thereof:

(2)

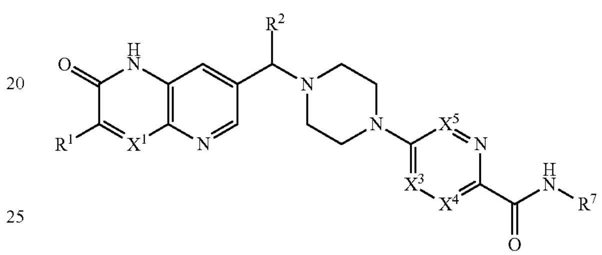

wherein in general formula (2):

$R^1$ is (C1-C4) alkyl, (C1-C4) fluoroalkyl, or (C3-C5) cycloalkyl;

$R^2$ is H or (C1-C3) alkyl;

One of $X^3$ and $X^4$ is CH, the other is N, $X^5$ is $CR^6$ or N, and $R^6$ is H, F, Cl, (C1-C4) alkyl, or (C1-C4) fluoroalkyl; or $X^3$ and $X^4$ are both CH, and $X^5$ is N; and $R^7$ is H, (C1-C4) alkyl or (C3-C4) cycloalkyl substituted with 0-2 F.

In another specific embodiment of the present invention, the compound of general formula (2) has one of the following structures:

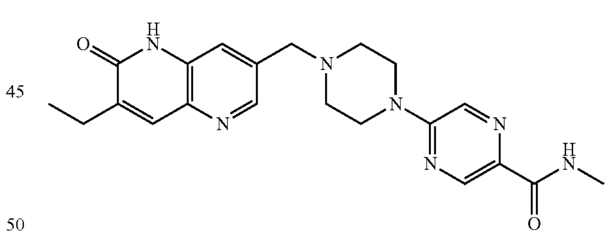

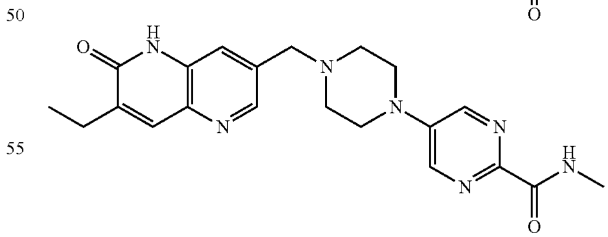

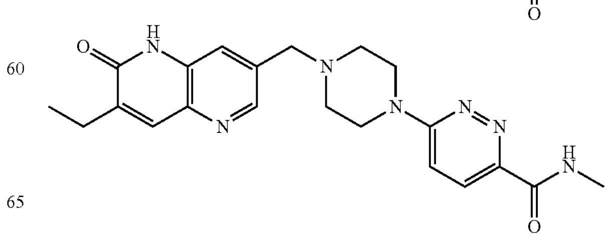

-continued

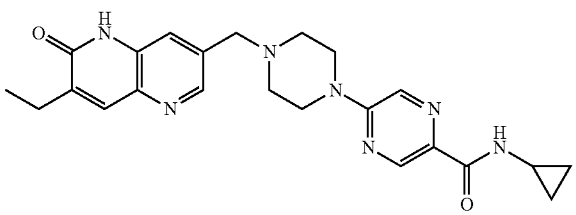

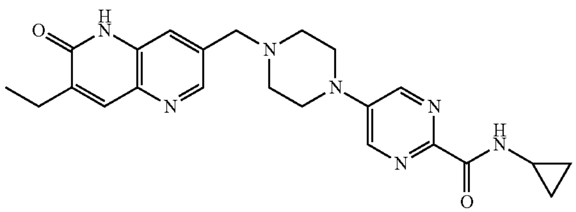

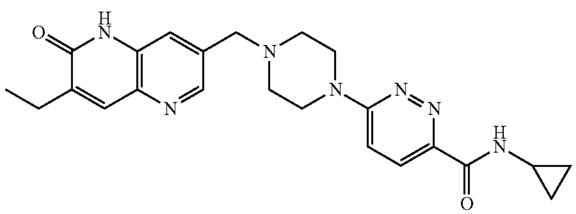

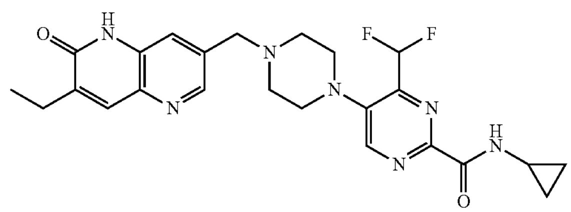

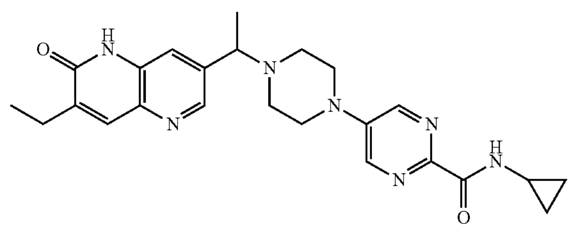

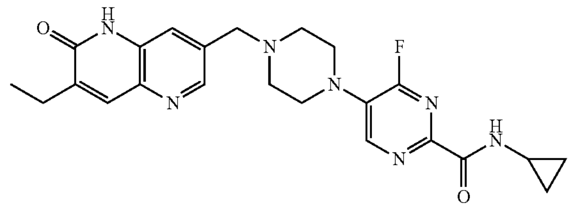

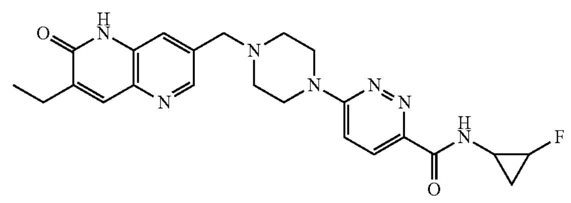

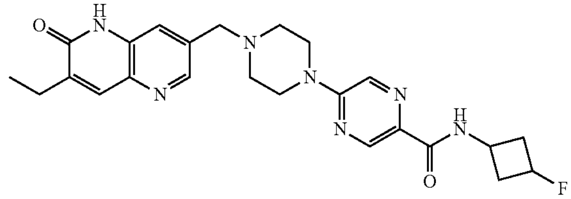

-continued

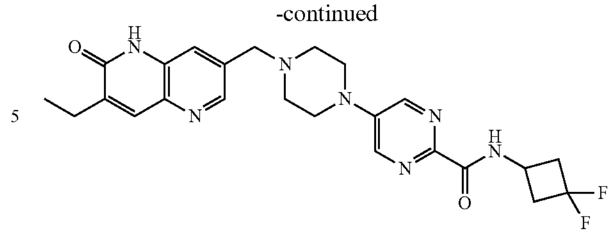

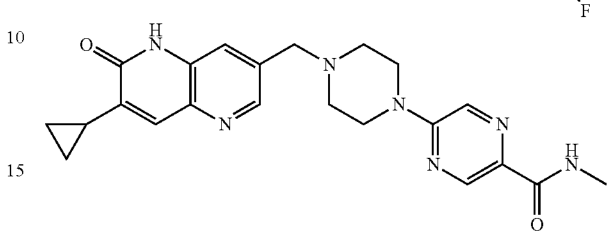

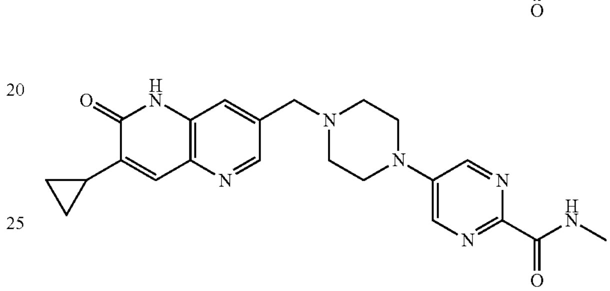

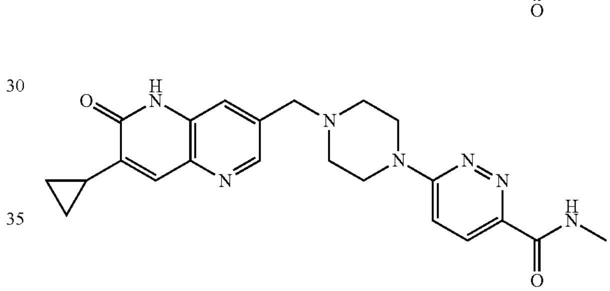

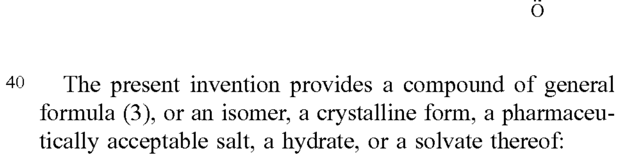

The present invention provides a compound of general formula (3), or an isomer, a crystalline form, a pharmaceutically acceptable salt, a hydrate, or a solvate thereof:

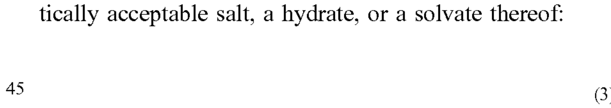

(3)

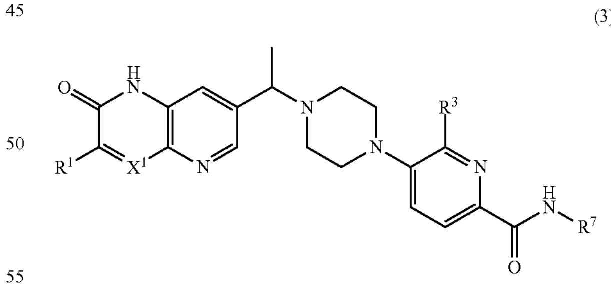

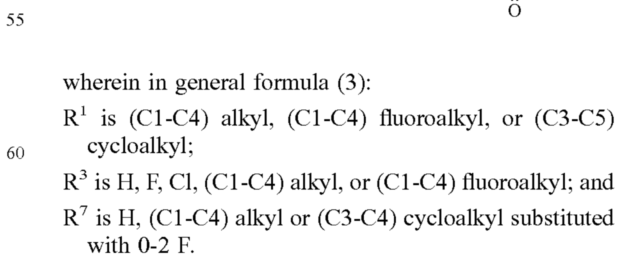

wherein in general formula (3):

$R^1$ is (C1-C4) alkyl, (C1-C4) fluoroalkyl, or (C3-C5) cycloalkyl;

$R^3$ is H, F, Cl, (C1-C4) alkyl, or (C1-C4) fluoroalkyl; and $R^7$ is H, (C1-C4) alkyl or (C3-C4) cycloalkyl substituted with 0-2 F.

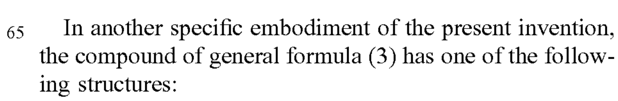

In another specific embodiment of the present invention, the compound of general formula (3) has one of the following structures:

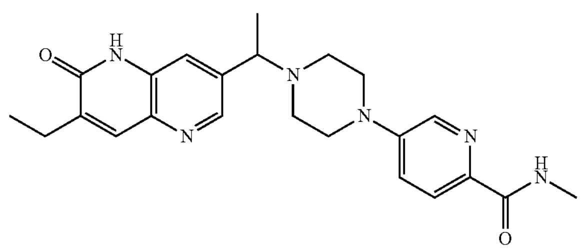

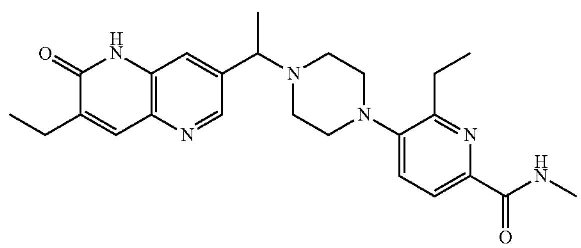

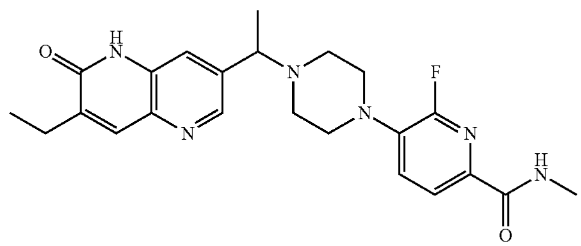

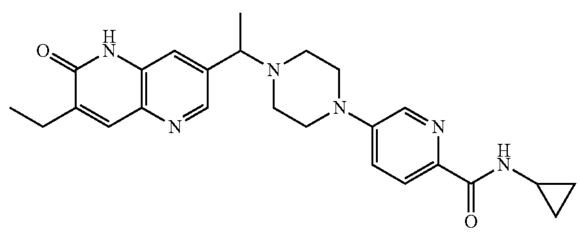

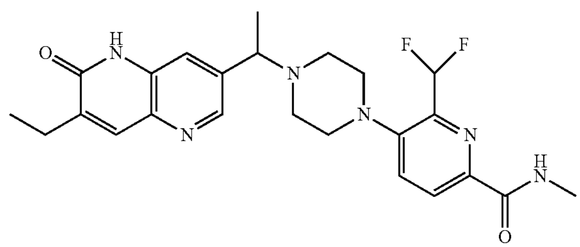

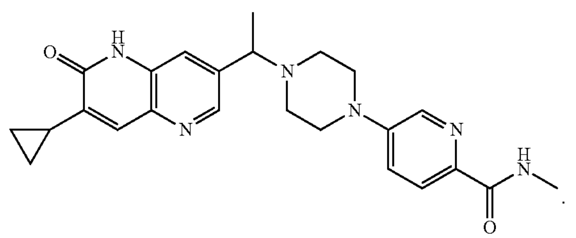

The present invention provides a compound of general formula (4), or an isomer, a crystalline form, a pharmaceutically acceptable salt, a hydrate, or a solvate thereof:

(4)

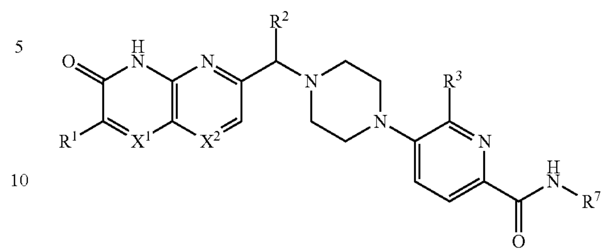

wherein in general formula (4):

$R^1$ is (C1-C4) alkyl, (C1-C4) fluoroalkyl, or (C3-C5) cycloalkyl;

$R^2$ is H or (C1-C3) alkyl;

$R^3$ is H, F, Cl, (C1-C4) alkyl, or (C1-C4) fluoroalkyl;

$R^7$ is H, (C1-C4) alkyl or (C3-C4) cycloalkyl substituted with 0-2 F; and $X^1$ and $X^2$ are each independently CH or N, but $X^1$ and $X^2$ are not both N.

In another specific embodiment of the present invention, the compound of general formula (4) has one of the following structures:

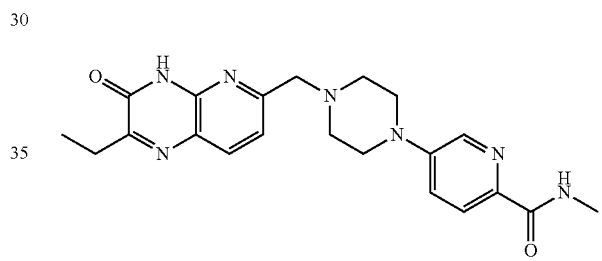

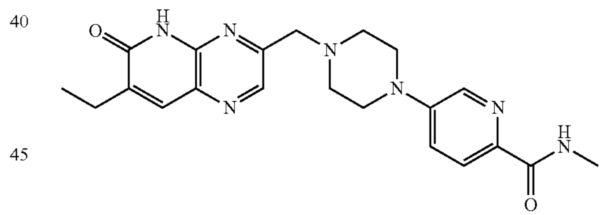

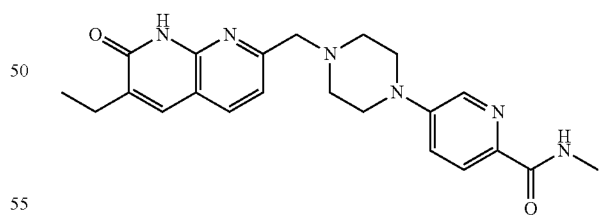

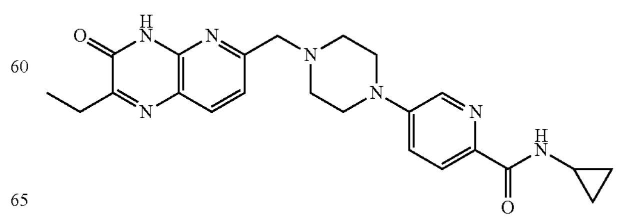

-continued

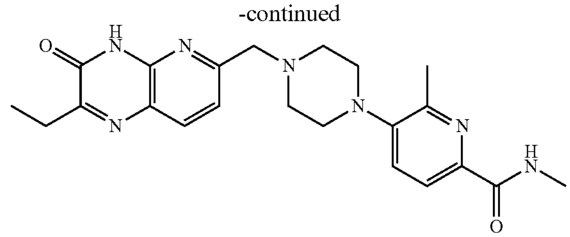

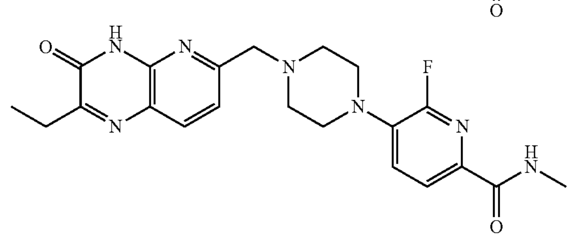

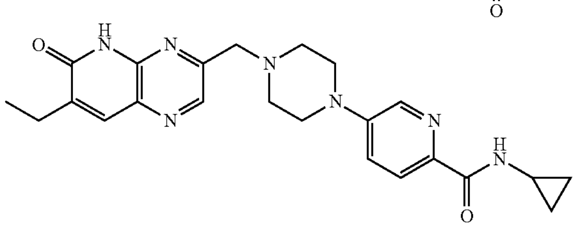

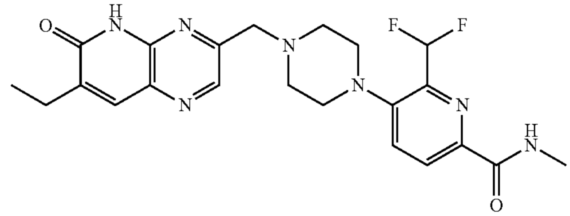

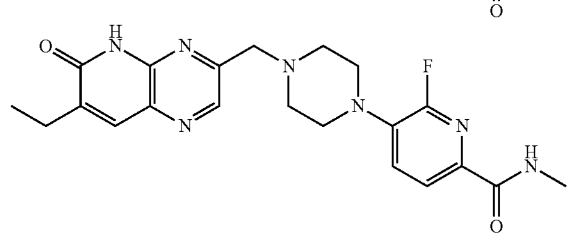

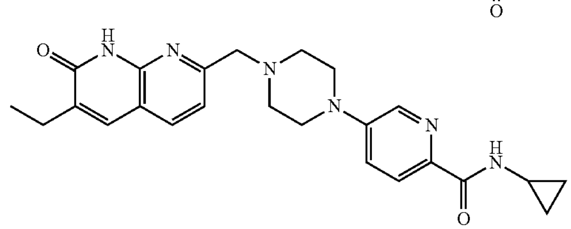

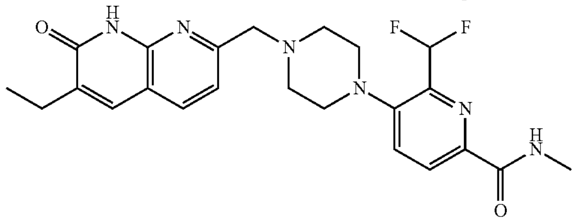

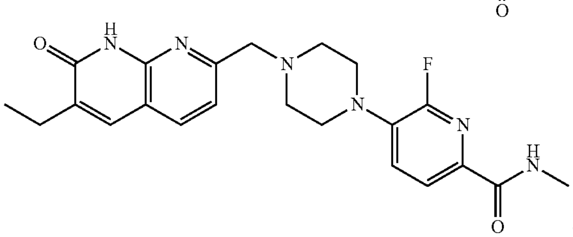

.

The present invention provides a compound of general formula (5), or an isomer, a crystalline form, a pharmaceutically acceptable salt, a hydrate, or a solvate thereof:

(5)

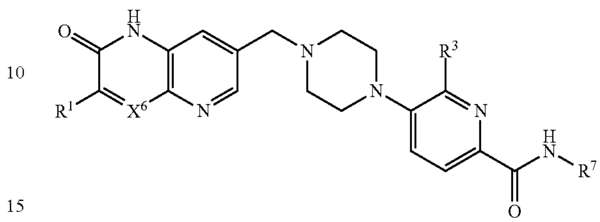

wherein in general formula (5):

$R^1$ is (C1-C4) alkyl, (C1-C4) fluoroalkyl, or (C3-C5) cycloalkyl;

$R^3$ is H, F, Cl, (C1-C4) alkyl, or (C1-C4) fluoroalkyl;

$R^7$ is H, (C1-C4) alkyl or (C3-C4) cycloalkyl substituted with 0-2 F; and $X^6$ is $NR^8$, O or $CR^9R^{10}$, $R^8$ is H or (C1-C3) alkyl, and $R^9$ and $R^{10}$ are each independently H, (C1-C3) alkyl, (C1-C3) fluoroalkyl, or (C3-C4) cycloalkyl.

In another specific embodiment of the present invention, the compound of general formula (5) has one of the following structures:

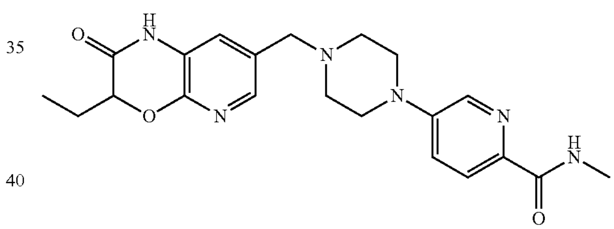

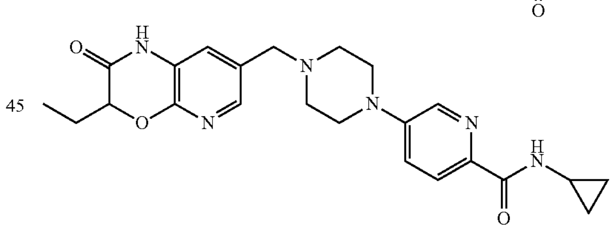

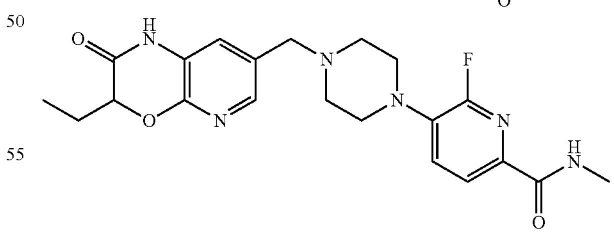

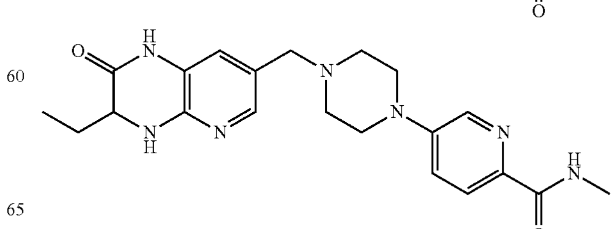

-continued

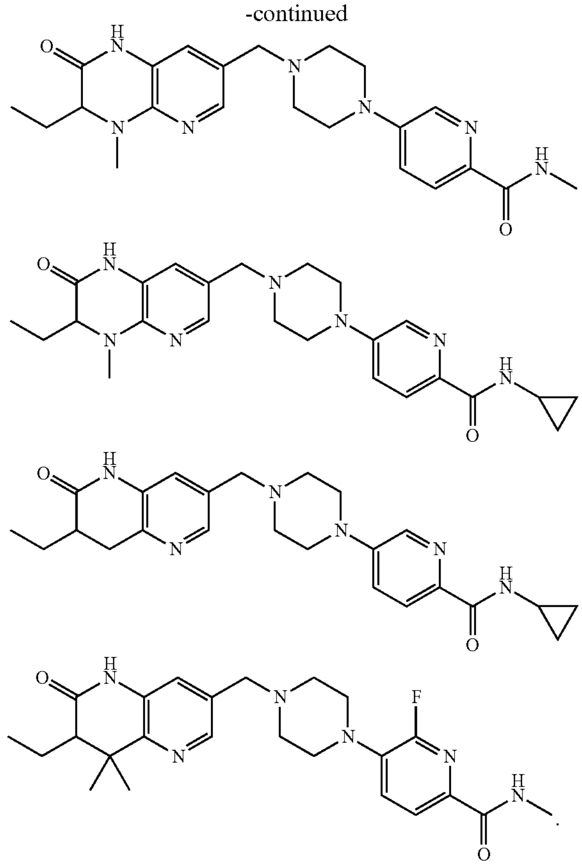

Another objective of the present invention is to provide a pharmaceutical composition comprising a pharmaceutically acceptable carrier, a diluent and/or an excipient and comprising the compounds of general formulas (1)-(5), or the isomers, the crystalline forms, the pharmaceutically acceptable salts, the hydrates or the solvates thereof of the present invention as an active ingredient.

Yet another objective of the present invention is to provide use of the compounds of general formulas (1)-(5), or the isomers, the crystalline forms, the pharmaceutically acceptable salts, the hydrates or the solvates thereof of the present invention or the pharmaceutical composition described above in the preparation of a medicament for treating, regulating or preventing diseases related to PARP.

Yet another objective of the present invention is to provide a method for treating, regulating or preventing related diseases mediated by PARP, the method including administering to a subject a therapeutically effective amount of the compounds of general formulas (1)-(5), or the isomers, the crystalline forms, the pharmaceutically acceptable salts, the hydrates or the solvates thereof of the present invention or the pharmaceutical composition described above.

It should be understood that both the above-mentioned general description and the following detailed description of the present invention are exemplary and explanatory, and are intended to provide further explanation of the present invention claimed.

Synthesis of Compounds

Methods for preparing the compounds of the general formulas of the present invention are specifically described below, but these specific methods do not limit the present invention in any way.

The compounds of the general formulas described above can be synthesized by using standard synthetic techniques or well-known techniques in combination with the methods described herein. In addition, solvents, temperatures and other reaction conditions mentioned herein may vary. Starting materials for the synthesis of the compounds can be obtained synthetically or commercially. The compounds described herein and other related compounds with different substituents can be synthesized by using well-known techniques and starting materials, including the methods found in March, ADVANCED ORGANIC CHEMISTRY, $4^{th}$ Ed., (Wiley 1992); Carey and Sundberg, ADVANCED ORGANIC CHEMISTRY, $4^{th}$ Ed., Vols. A and B (Plenum 2000, 2001); and Green and Wuts, PROTECTIVE GROUPS IN ORGANIC SYNTHESIS, $3^{rd}$ Ed., (Wiley 1999). General methods for preparing the compounds can be modified by using appropriate reagents and conditions for introducing different groups into the molecular formulas provided herein.

In one aspect, the compounds described herein are prepared according to methods well known in the art. However, the conditions of the methods, such as reactants, solvents, bases, the amount of the compounds used, reaction temperature and time required for the reaction are not limited to the following explanation. The compounds of the present invention can also be conveniently prepared by optionally combining various synthetic methods described herein or known in the art, and such combinations can be easily carried out by those skilled in the art to which the present invention pertains. In one aspect, the present invention further provides a method for preparing the compound of general formula (1), which is prepared using general reaction schemes 1-5 below.

General Reaction Scheme 1

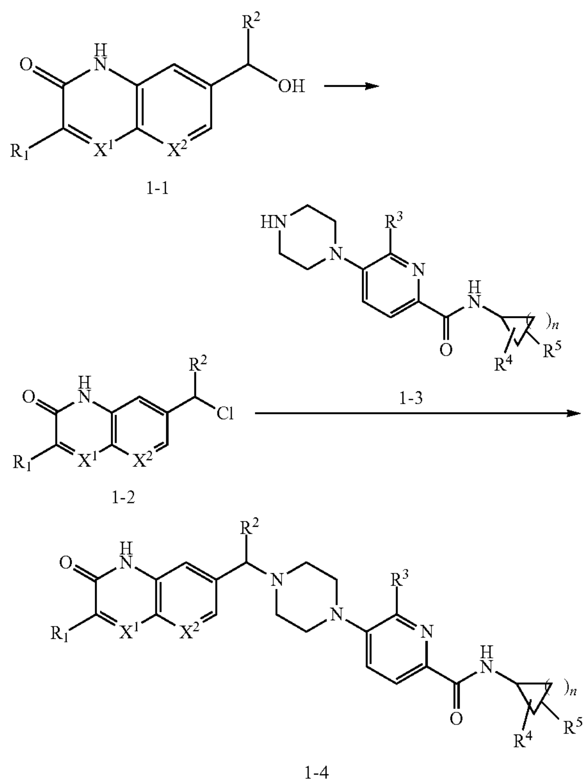

1-1

1-3

1-2

1-4

Embodiments of the compound of general formula (1) may be prepared according to general reaction scheme 1, wherein $R^1$, $R^2$, $R^3$, $R^4$, $R^5$, $X^1$, $X^2$ and n are as defined above. As shown in general reaction scheme 1, compound 1-1 reacts with thionyl chloride to generate compound 1-2, and compound 1-2 and compound 1-3 are subjected to a substitution reaction to generate target compound 1-4.

General Reaction Scheme 2

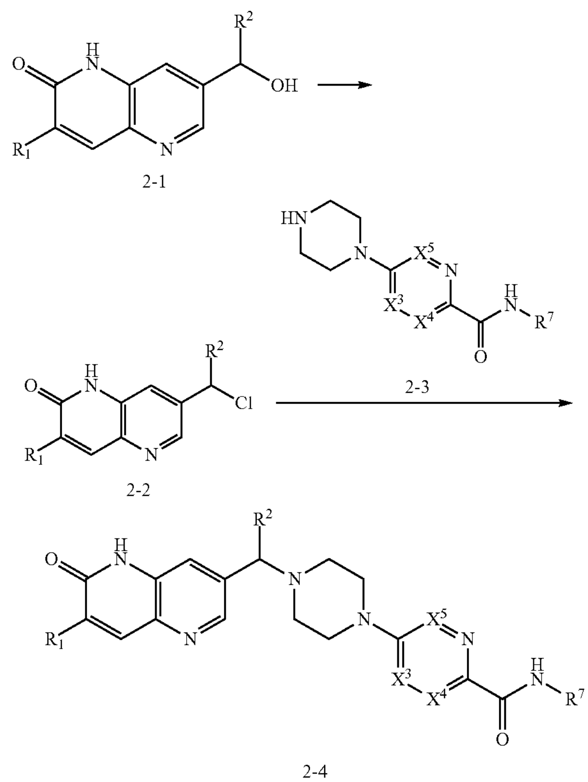

2-1

2-3

2-2

2-4

Embodiments in the compound of general formula (2) may be prepared according to general reaction scheme 2, wherein $R^1$, $R^2$, $R^7$, $X^3$, $X^4$ and $X^5$ are as defined above. As shown in general reaction scheme 2, compound 2-1 reacts with thionyl chloride to generate compound 2-2, and compound 2-2 and compound 2-3 are subjected to a substitution reaction to generate target compound 2-4.

General Reaction Scheme 3

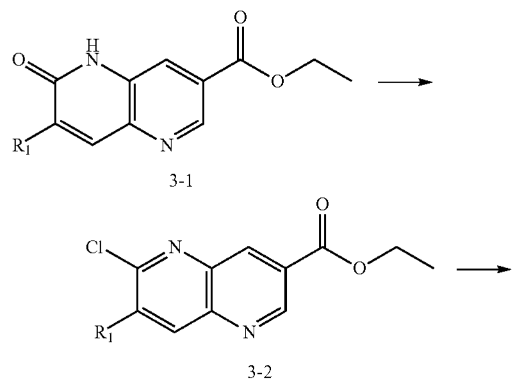

3-1

3-2

-continued

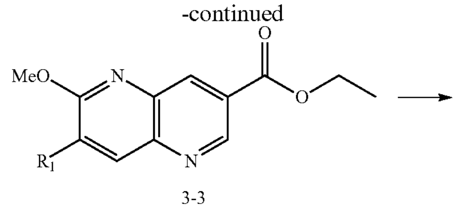

3-3

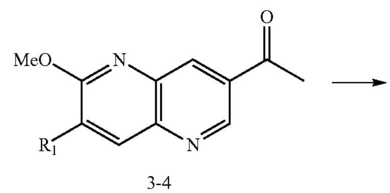

3-4

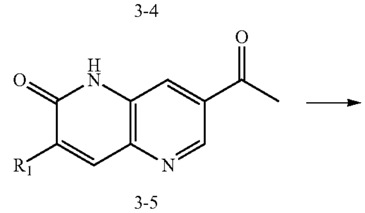

3-5

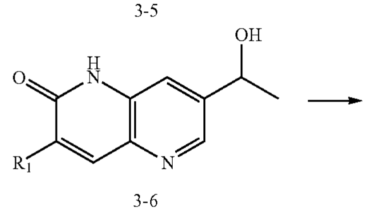

3-6

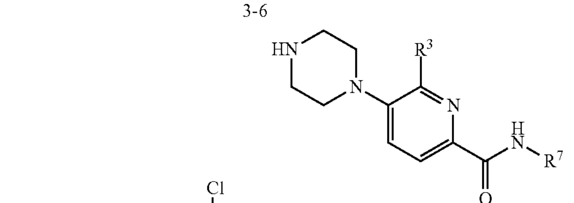

3-8

3-7

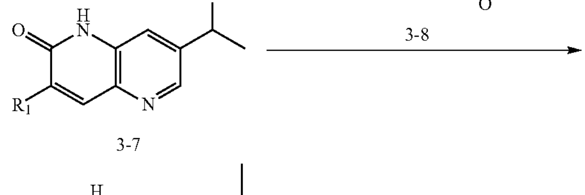

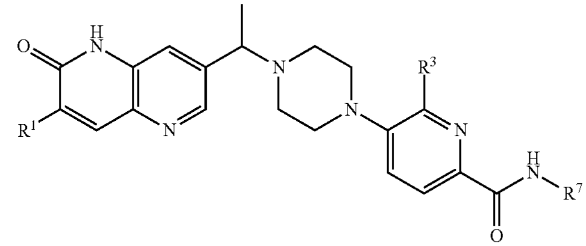

3-9

Embodiments of the compound of general formula (3) may be prepared according to general reaction scheme 3, wherein $R^1$, $R^3$ and $R^7$ are as defined above. As shown in general reaction scheme 3, compound 3-1 reacts with phosphorus oxychloride to generate compound 3-2, compound 3-2 reacts with sodium methoxide to generate compound 3-3, compound 3-3 reacts with methyllithium at a low temperature to generate compound 3-4, compound 3-4 generates compound 3-5 under the action of hydrochloric acid, compound 3-5 is reduced by a reducing agent to generate compound 3-6, compound 3-6 reacts with the thionyl chloride to generate compound 3-7, and compound 3-7 and compound 3-8 are subjected to a substitution reaction to generate target compound 3-9.

General Reaction Scheme 4

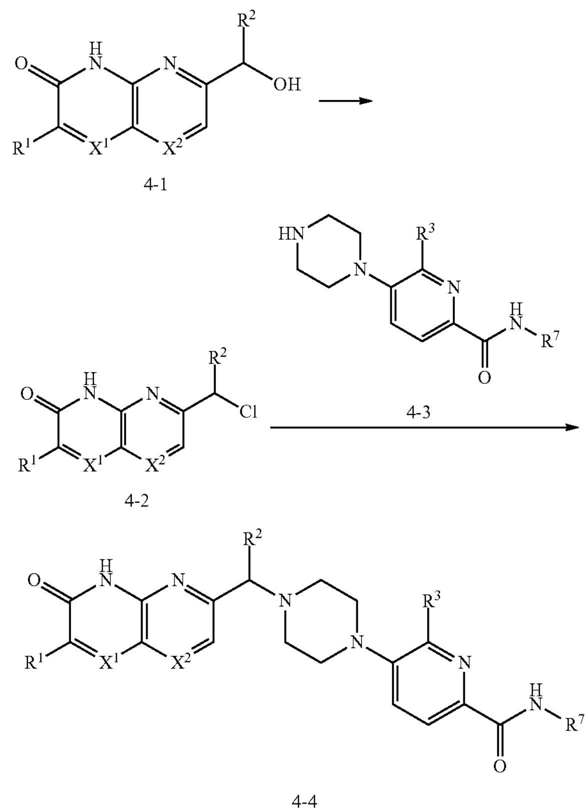

4-1

4-3

4-2

4-4

Embodiments of the compound of general formula (4) may be prepared according to general reaction scheme 4, wherein $R^1$, $R^2$, $R^3$, $R^7$, $X^1$ and $X^2$ are as defined above. As shown in general reaction scheme 4, compound 4-1 reacts with thionyl chloride to generate compound 4-2, and compound 4-2 and compound 4-3 are subjected to a substitution reaction to generate target compound 4-4.

General Reaction Scheme 5

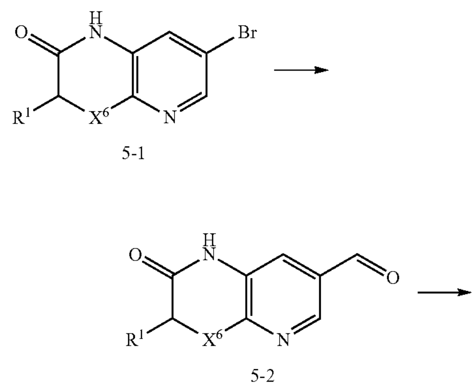

5-1

5-2

-continued

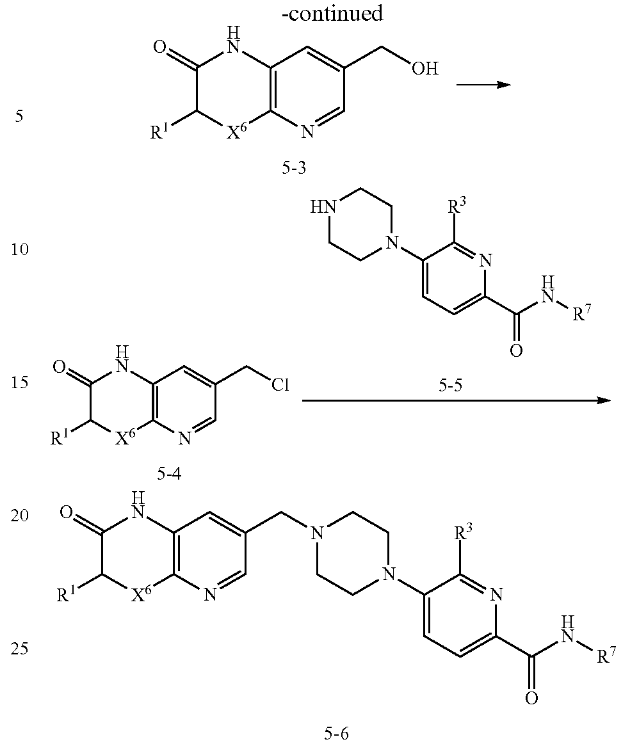

5-3

5-5

5-4

5-6

Embodiments of the compound of general formula (5) may be prepared according to general reaction scheme 5, wherein $R^1$, $R^3$, $R^7$ and $X^6$ are as defined above. As shown in general reaction scheme 5, compound 5-1 is subjected to a carbonylation reaction in the presence of a reducing agent (e.g., triethylsilane) to obtain compound 5-2, compound 5-2 is reduced by a reducing agent to generate compound 5-3, compound 5-3 reacts with thionyl chloride to generate compound 5-4, and compound 5-4 and compound 5-5 are subjected to a substitution reaction to generate target compound 5-6.

Further Forms of Compounds

"Pharmaceutically acceptable" herein means a substance, such as a carrier or a diluent, which will not lead to loss of biological activity or properties of a compound and is relatively non-toxic. For example, when an individual is given a substance, the substance will not cause undesired biological effects or interact with any component contained therein in a deleterious manner.

The term "pharmaceutically acceptable salt" means an existing form of a compound, that does not cause significant irritation to the organism receiving the administration or eliminate the biological activity and properties of the compound. In certain specific aspects, the pharmaceutically acceptable salt is obtained by subjecting the compound of the general formula to a reaction with acids, e.g., inorganic acids such as hydrochloric acid, hydrobromic acid, hydrofluoric acid, sulfuric acid, phosphoric acid, nitric acid, carbonic acid and the like, organic acids such as formic acid, acetic acid, propionic acid, oxalic acid, trifluoroacetic acid, malonic acid, succinic acid, fumaric acid, maleic acid, lactic acid, malic acid, tartaric acid, citric acid, picric acid, methanesulfonic acid, benzenesulfonic acid, p-toluenesulfonic acid and the like, and acidic amino acids such as aspartic acid, glutamic acid and the like.

It should be understood that references to pharmaceutically acceptable salts include solvent addition forms or crystalline forms, especially solvates or polymorphs. A solvate contains either stoichiometric or non-stoichiometric amount of solvent and is selectively formed during crystallization in a pharmaceutically acceptable solvent such as water and ethanol. Hydrates are formed when the solvent is water, or alcoholates are formed when the solvent is ethanol. The solvates of the compound of the general formula are conveniently prepared or formed according to the methods described herein. For example, hydrates of the compound of the general formula are conveniently prepared by recrystallization in a mixed solvent of water/organic solvent, wherein the organic solvent used includes, but is not limited to, tetrahydrofuran, acetone, ethanol or methanol. In addition, the compounds described herein may be present in either a non-solvated form or a solvated form. In general, the solvated forms are considered equivalent to the non-solvated forms for purposes of the compounds and methods provided herein.

In other specific embodiments, the compound of the general formula is prepared in different forms including, but not limited to, amorphous, pulverized and nanoparticle forms. In addition, the compound of the general formula includes crystalline forms, and may also be polymorphs. Polymorphs include different lattice arrangements of the same elements of a compound. The polymorphs generally have different X-ray diffraction spectra, infrared spectra, melting points, density, hardness, crystalline forms, optical and electrical properties, stability and solubility. Different factors such as a recrystallization solvent, crystallization rate and storage temperature may lead to a single dominant crystalline form.

In another aspect, the compound of the general formula may have a chiral center and/or axial chirality, and therefore may be present in the form of a racemate, a racemic mixture, a single enantiomer, a diastereomeric compound, a single diastereomer and a cis-trans isomer. Each chiral center or axial chirality will independently produce two optical isomers, and all possible optical isomers, diastereomeric mixtures and pure or partially pure compounds are included within the scope of the present invention. The present invention is meant to include all such isomeric forms of these compounds.

The compound of the present invention may contain unnatural proportions of atomic isotopes at one or more of the atoms that constitute the compound. For example, the compound may be labeled with radioactive isotopes, such as tritium ($^3H$), iodine-125 ($^{125}I$) and C-14 ($^{14}C$). For another example, deuterium can be used to substitute a hydrogen atom to form a deuterated compound. The bond formed by deuterium and carbon is stronger than that formed by ordinary hydrogen and carbon. Compared with an undeuterated medicament, the deuterated medicament generally has the advantages of reduced adverse effects, increased medicament stability, enhanced efficacy, prolonged in vivo half-life and the like. All isotopic variations of the compound of the present invention, whether radioactive or not, are contained within the scope of the present invention.

Terminology

Unless otherwise stated, the terms used in the present invention, including those in the specification and claims, are defined as follows. It must be noted that in the specification and the appended claims, the singular forms "a" and "an" include plural meanings unless clearly indicated otherwise. Unless otherwise stated, conventional methods for mass spectrometry, nuclear magnetic resonance spectroscopy, HPLC, protein chemistry, biochemistry, recombinant DNA technology and pharmacology are used. As used herein, "or" or "and" used refers to "and/or" unless otherwise stated.

Unless otherwise specified, "alkyl" refers to a saturated aliphatic hydrocarbon group, including linear and branched groups containing 1 to 6 carbon atoms. Lower alkyl groups containing 1 to 4 carbon atoms, such as methyl, ethyl, propyl, 2-propyl, n-butyl, isobutyl or tert-butyl, are preferred. As used herein, "alkyl" includes unsubstituted and substituted alkyl, particularly alkyl substituted with one or more halogens. Preferred alkyl is selected from $CH_3$, $CH_3CH_2$, $CF_3$, $CHF_2$, $CF_3CH_2$, $CF_3(CH_3)CH$, $^{i}$Pr, $^{n}$Pr, $^{i}$Bu, $^{n}$Bu or $^{t}$Bu.

Unless otherwise specified, "cycloalkyl" refers to a non-aromatic hydrocarbon ring system (monocyclic, bicyclic or polycyclic), and partially unsaturated cycloalkyl may be referred to as "cycloalkenyl" if the carbocyclic ring contains at least one double bond, or "cycloalkynyl" if the carbocyclic ring contains at least one triple bond. The cycloalkyl may include monocyclic or polycyclic groups and spiro rings (e.g., having 2, 3 or 4 fused rings). In some embodiments, the cycloalkyl is monocyclic. In some embodiments, the cycloalkyl is monocyclic or bicyclic. The ring carbon atoms of the cycloalkyl may optionally be oxidized to form an oxo or sulfido group. The cycloalkyl further includes cycloalkylene. In some embodiments, the cycloalkyl contains 0, 1 or 2 double bonds. In some embodiments, the cycloalkyl contains 1 or 2 double bonds (partially unsaturated cycloalkyl). In some embodiments, the cycloalkyl may be fused to aryl, heteroaryl, cycloalkyl and heterocycloalkyl. In some embodiments, the cycloalkyl may be fused to aryl, cycloalkyl and heterocycloalkyl. In some embodiments, the cycloalkyl may be fused to aryl and heterocycloalkyl. In some embodiments, the cycloalkyl may be fused to aryl and cycloalkyl. Examples of the cycloalkyl include cyclopropyl, cyclobutyl, cyclopentyl, cyclohexyl, cycloheptyl, cyclopentenyl, cyclohexenyl, cyclohexadienyl, cycloheptatrienyl, norcamphanyl, norpinanyl, norcarnyl, bicyclo[1.1.1]pentyl, bicyclo[2.1.1]hexyl and the like.

Unless otherwise specified, "alkoxy" refers to an alkyl group that bonds to the rest of the molecule through an ether oxygen atom. Representative alkoxy groups are those having 1-6 carbon atoms, such as methoxy, ethoxy, propoxy, isopropoxy, butoxy, isobutoxy, sec-butoxy and tert-butoxy. As used herein, "alkoxy" includes unsubstituted and substituted alkoxy, particularly alkoxy substituted with one or more halogens. Preferred alkoxy is selected from $OCH_3$, $OCF_3$, $CHF_2O$, $CF_3CH_2O$, $^{i-}$PrO, $^{n-}$PrO, $^{i-}$BuO, $^{n-}$BuO or $^{i-}$BuO.

Unless otherwise specified, "halogen" (or halo) refers to fluorine, chlorine, bromine or iodine. The term "halo" (or "halogenated") before a group name indicates that the group is partially or fully halogenated, that is, substituted in any combination with F, Cl, Br or I, preferably with F or Cl.

"Optional" or "optionally" means that the subsequently described event or circumstance may, but does not necessarily, occur, and the description includes instances where the event or circumstance occurs and instances where the event or the circumstance does not occur.

The substituent "—O—$CH_2$—O—" means that two oxygen atoms in the substituent are linked to two adjacent carbon atoms in the heterocycloalkyl, aryl or heteroaryl, for example:

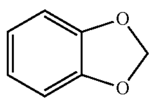

When the number of a linker group is 0, such as $—(CH_2)_0—$, it means that the linker group is a single bond.

When one of the variables is selected from a chemical bond, it means that the two groups linked by this variable are linked directly. For example, when L in X-L-Y represents a chemical bond, it means that the structure is actually X—Y.

The term "membered ring" includes any cyclic structure. The term "membered" is intended to refer to the number of backbone atoms that form a ring. For example, cyclohexyl, pyridinyl, pyranyl and thiopyranyl are six-membered rings, and cyclopentyl, pyrrolyl, furanyl and thienyl are five-membered rings.

The term "moiety" refers to a specific portion or functional group of a molecule. A chemical moiety is generally considered to be a chemical entity contained in or attached to the molecule. Unless otherwise stated, a wedged solid bond ( ) and a wedged dashed bond () represent the absolute configuration of a stereogenic center, and a straight solid bond ( ) and a straight dashed bond () represent the relative configuration of the stereogenic center. A wavy line ( ) represents a wedged solid bond () or a wedged dashed bond ( ), or a wavy line ( ) represents a straight solid bond ( ) or a straight dashed bond ( ).

Unless otherwise stated, a single bond or a double bond is represented by  .

Specific Pharmaceutical and Medical Terminology

The term "acceptable", as used herein, means that a formulation component or an active ingredient does not unduly and adversely affect a general therapeutic target's health.

The terms "treatment," "treatment course" and "therapy", as used herein, include alleviating, inhibiting or improving a symptom or condition of a disease; inhibiting the development of complications; improving or preventing underlying metabolic syndrome; inhibiting the development of a disease or symptom, e.g., controlling the progression of a disease or condition; alleviating a disease or symptom; leading to disease or symptom regression; and alleviating a complication caused by a disease or symptom, or preventing or treating a sign caused by a disease or symptom. As used herein, a compound or pharmaceutical composition, when administered, can improve a disease, a symptom or a condition, which particularly means improving the severity, delaying the onset, slowing the progression, or reducing the duration of the disease. Fixed or temporary administration, or continuous or intermittent administration, may be attributed to or associated with the administration.

"Active ingredient" refers to the compound of the general formula, and pharmaceutically acceptable inorganic or organic salts of the compound of the general formula. The compound of the present invention may contain one or more asymmetric centers (chiral center or axial chirality) and thus occur in the form of a racemate, a racemic mixture, a single enantiomer, a diastereomeric compound and a single diastereomer. Asymmetric centers that may be present depend on the nature of the various substituents on the molecule. Each of such asymmetric centers will independently produce two optical isomers, and all possible optical isomers, diastereomeric mixtures and pure or partially pure compounds are included within the scope of the present invention. The present invention is meant to include all such isomeric forms of these compounds.

The terms such as "compound", "composition", "agent" or "medicine or medicament" are used interchangeably herein and all refer to a compound or composition that, when administered to an individual (human or animal), can induce a desired pharmacological and/or physiological response by local and/or systemic action.

The term "administered, administering or administration" herein means the direct administration of the compound or the composition, or the administration of a prodrug, a derivative, an analog or the like of the active compound.

Although the numerical ranges and parameters defining the broad scope of the present invention are approximations, the related numerical values set forth in the specific examples have been presented herein as precisely as possible. Any numerical value, however, inherently contains a standard deviation necessarily resulting from certain methods for testing. Herein, "about" generally means that the actual value is within a particular value or range ±10%, 5%, 1% or 0.5%. Alternatively, the term "about" indicates that the actual numerical value falls within the acceptable standard error of a mean, as considered by those skilled in the art. All ranges, quantities, numerical values and percentages used herein (e.g., to describe an amount of a material, a length of time, a temperature, an operating condition, a quantitative ratio and the like) are to be understood as being modified by the word "about", except in the experimental examples or where otherwise explicitly indicated. Accordingly, unless otherwise contrarily stated, the numerical parameters set forth in the specification and the appended claims are all approximations that may vary as desired. At least, these numerical parameters should be understood as the significant digits indicated or the numerical values obtained using conventional rounding rules.

Unless otherwise defined in the specification, the scientific and technical terms used herein have the same meaning as commonly understood by those skilled in the art. In addition, nouns in their singular forms used in the specification encompass their plural forms, unless contradicted by context; and nouns in their plural forms used also encompass their singular forms.

Therapeutic Use

The present invention provides a method for treating a disease, including but not limited to a condition involving PARP (e.g., cancer), with the compound or pharmaceutical composition of the general formula of the present invention.

In some embodiments, a method for treating cancer is provided, the method including administering to an individual in need thereof an effective amount of any above-mentioned pharmaceutical composition including the compound of a structural general formula. In some embodiments, the cancer is mediated by PARP. In other embodiments, the cancer is a hematologic cancer and a solid tumor, including but not limited to, leukemia, breast cancer, lung cancer, pancreatic cancer, colon cancer, bladder cancer, brain cancer, urothelial cancer, prostate cancer, liver cancer, ovarian cancer, head and neck cancer, gastric cancer, mesothelioma or all cancer metastases.

Route of Administration

The compound and the pharmaceutically acceptable salt thereof of the present invention can be made into various formulations including a safe and effective amount of the compound or the pharmaceutically acceptable salt thereof of the present invention, and a pharmaceutically acceptable excipient or carrier, wherein the "safe and effective amount" means that the amount of the compound is sufficient to significantly improve the condition without causing serious adverse effects. The safe and effective amount of the compound is determined according to the age, condition, course of treatment and other specific conditions of a treated subject.

"Pharmaceutically acceptable excipient or carrier" refers to one or more compatible solid or liquid fillers or gel substances that are suitable for human use and must be of sufficient purity and sufficiently low toxicity. "Compatible" herein means that the components of the composition can intermix with the compound of the present invention and with each other, without significantly reducing the pharmaceutical efficacy of the compound. Examples of pharmaceutically acceptable excipients or carriers include cellulose and derivatives thereof (e.g., sodium carboxymethylcellulose, sodium ethylcellulose or cellulose acetate), gelatin, talc, solid lubricants (e.g., stearic acid or magnesium stearate), calcium sulfate, vegetable oil (e.g., soybean oil, sesame oil, peanut oil or olive oil), polyols (e.g., propylene glycol, glycerol, mannitol or sorbitol), emulsifiers (e.g., Tween®), wetting agents (e.g., sodium lauryl sulfate), colorants, flavoring agents, stabilizers, antioxidants, preservatives, pyrogen-free water and the like.

When the compound of the present invention is administered, it may be administered orally, rectally, parenterally (intravenously, intramuscularly or subcutaneously) or topically.

Solid dosage forms for oral administration include capsules, tablets, pills, pulvises and granules. In these solid dosage forms, the active compound is mixed with at least one conventional inert excipient (or carrier), such as sodium citrate or dicalcium phosphate, or with the following ingredients: (a) fillers or extenders, such as starch, lactose, sucrose, glucose, mannitol and silicic acid; (b) binders, such as hydroxymethyl cellulose, alginate, gelatin, polyvinylpyrrolidone, sucrose and acacia; (c) humectants, such as glycerol; (d) disintegrants, such as agar, calcium carbonate, potato starch or tapioca starch, alginic acid, certain complex silicates and sodium carbonate; (e) solution retarders, such as paraffin; (f) absorption accelerators, such as quaternary ammonium compounds; (g) wetting agents, such as cetyl alcohol and glycerol monostearate; (h) adsorbents, such as kaolin; and (i) lubricants, such as talc, calcium stearate, magnesium stearate, solid polyethylene glycol and sodium lauryl sulfate, or mixtures thereof. In the case of capsules, tablets and pills, the dosage forms may further include buffers.

Solid dosage forms such as tablets, dragees, capsules, pills and granules may be prepared using coatings and shells such as enteric coatings and other materials well known in the art. They may include opacifying agents, and the active compound or compound in such composition may be released in a certain part of the digestive tract in a delayed manner. Examples of embedding components that can be used are polymeric substances and wax-based substances. If necessary, the active compound can also be in microcapsule form with one or more of the excipients described above.

Liquid dosage forms for oral administration include pharmaceutically acceptable emulsions, solutions, suspensions, syrups or elixirs. In addition to the active compound, the liquid dosage form may include inert diluents commonly used in the art, such as water or other solvents, solubilizers and emulsifiers, for example, ethanol, isopropanol, ethyl carbonate, ethyl acetate, propylene glycol, 1,3-butanediol, dimethylformamide and oils, especially cottonseed oil, peanut oil, corn germ oil, olive oil, castor oil and sesame oil, or mixtures of these substances.

Besides such inert diluents, the composition may further comprise adjuvants, such as wetting agents, emulsifiers, suspending agents, sweeteners, flavoring agents and perfuming agents.

In addition to the active compound, the suspensions may include suspending agents, such as ethoxylated isostearyl alcohols, polyoxyethylene sorbitol and sorbitan esters, microcrystalline cellulose, aluminum methylate and agar, or mixtures of these substances.

Compositions for parenteral injection may include physiologically acceptable sterile aqueous or anhydrous solutions, dispersions, suspensions or emulsions, and sterile powders for redissolving into sterile injectable solutions or dispersions. Suitable aqueous and non-aqueous carriers, diluents, solvents or excipients include water, ethanol, polyols and suitable mixtures thereof. Dosage forms for topical administration of the compound of the present invention include ointments, pulvises, patches, sprays and inhalants. The active ingredient is mixed under sterile conditions with a physiologically acceptable carrier and any preservatives, buffers or propellants that may be required if necessary.

The compound of the present invention may be administered alone or in combination with other pharmaceutically acceptable compounds. When the pharmaceutical composition is used, a safe and effective amount of the compound of the present invention is administered to a mammal (such as a human) to be treated, wherein the dose of administration is a pharmaceutically effective dose. For a human of 60 kg, the daily dose of administration is usually 1-2000 mg, preferably 50-1000 mg. Certainly, in a specific dose, such factors as the route of administration, the health condition of the patient and the like will also be considered, which are well known to skilled physicians.

The features mentioned in the present invention or those mentioned in the examples may be combined arbitrarily. All the features disclosed in this specification may be used with any composition form and the various features disclosed in this specification may be replaced with any alternative features that provide the same, equivalent or similar purpose. Thus, unless otherwise specified, the features disclosed herein are merely general examples of equivalent or similar features.

DETAILED DESCRIPTION

Various specific aspects, features and advantages of the compounds, methods and pharmaceutical compositions described above will be set forth in detail in the following description, which will make the content of the present invention very clear. It should be understood that the detailed description and examples below describe specific examples for reference only. After reading the description of the present invention, those skilled in the art can make various changes or modifications to the present invention, and such equivalents also fall within the scope of the present application defined herein.

In all examples, $^{1}$H-NMR spectra were recorded with a Varian Mercury 400 nuclear magnetic resonance spectrometer, and chemical shifts are expressed in δ (ppm); silica gel for separation was 200-300 mesh silica gel if not specified, and the ratio of the eluents was a volume ratio.

Example 1. Synthesis of Compound 1

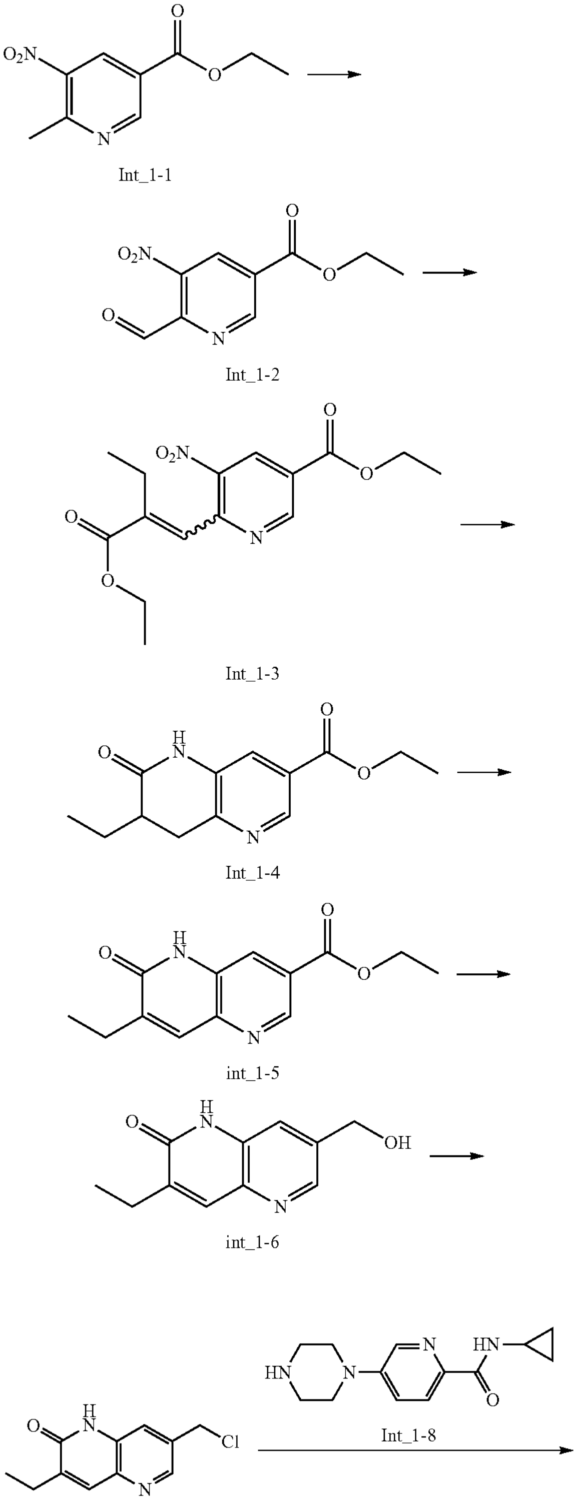

Int_1-1

Int_1-2

Int_1-3

Int_1-4 int_1-5 int_1-6

Int_1-8 int_1-7

-continued

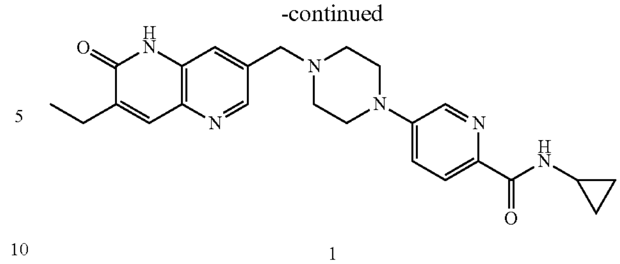

1

Step 1: Synthesis of Compound Int_1-2

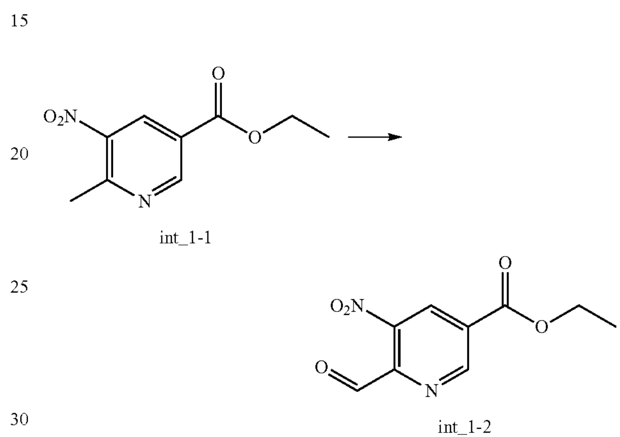

int_1-1 int_1-2

Selenium dioxide (3.96 g, 35.68 mmol) was added to a solution of compound nt_1-1 (5.00 g, 23.79 mmol) in dioxane (30 mL) at room temperature, and the reaction solution was heated to 110° C. and stirred for 20 h. After being cooled, the reaction solution was filtered through diatomite, and the filter cake was washed with ethyl acetate (100 mL). The filtrates were combined and concentrated under reduced pressure, and the residue was separated and purified by silica gel chromatography to obtain intermediate int_1-2.

LC-MS (ESI): 225 $[M+H]^+$.

Step 2: Synthesis of Compound Int_1-3

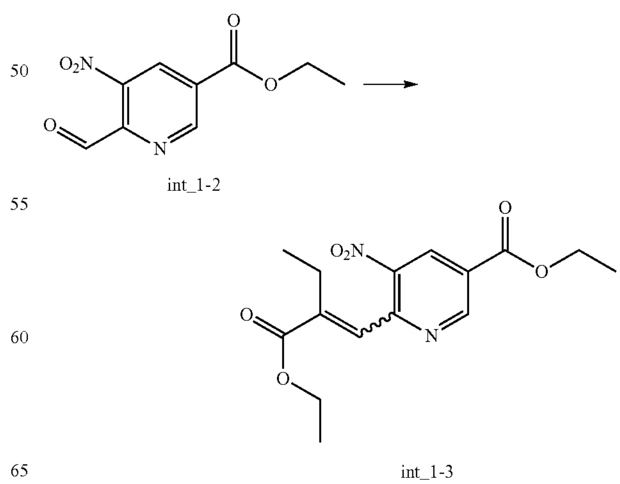

int_1-2 int_1-3

Triethyl 2-phosphonobutyrate (14.07 g, 55.76 mmol) was slowly added dropwise to a solution of 60% sodium hydride (2.23 g, 55.76 mmol) in anhydrous tetrahydrofuran (25 mL) with stirring at 0 °C. After the completion of dropwise addition, the mixture was stirred at 0 °C for 10 min, slowly warmed to room temperature, then heated to 40 °C and stirred for 5 min. The reaction solution was cooled to −78 °C, and a solution of intermediate int_1-2 (5.00 g, 22.30 mmol) in anhydrous tetrahydrofuran (25 mL) was slowly added dropwise with stirring. The mixture was quenched by adding a saturated aqueous ammonium chloride solution (100 mL), and the reaction solution was concentrated under reduced pressure to remove most of tetrahydrofuran, and extracted with ethyl acetate (150 mL×2). The organic phases were combined, washed with water (50 mL), washed with saturated brine (50 mL), dried over anhydrous sodium sulfate and filtered.

The filtrate was concentrated under reduced pressure, and the residue was separated and purified by silica gel chromatography to obtain intermediate int_1-3 (a mixture of E/Z configuration).

LC-MS (ESI): 323 $[M+H]^+$.

Step 3: Synthesis of Compound Int 1-4

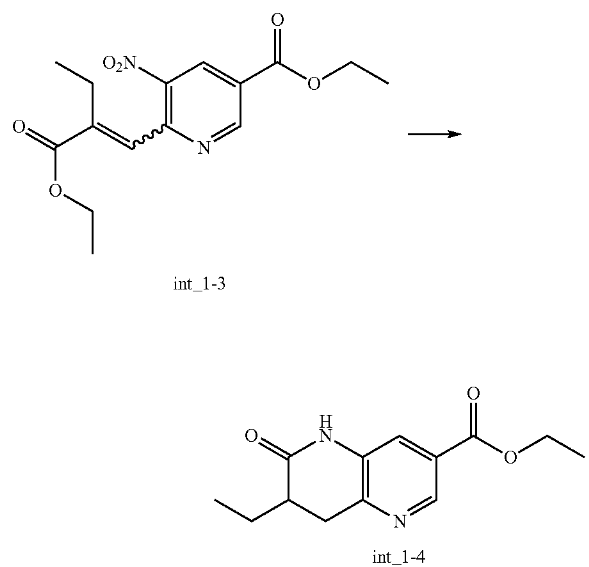

int_1-3 int_1-4

Intermediate int_1-3 (3.00 g, 9.31 mmol) and palladium on carbon (10%, water content of 50%, 1.49 g) were mixed in ethanol (25 mL), and after the mixture was purged with hydrogen 2 times, the reaction mixture was stirred under hydrogen atmosphere (hydrogen balloon) at room temperature overnight. The mixture was filtered, the filtrate was concentrated under reduced pressure, a solution of hydrogen chloride in dioxane (4 M, 10 mL) was added, and the resulting mixture was stirred at room temperature for 0.5 h. Diethyl ether (100 mL) was added for dilution, the mixture was filtered, and the filter cake was washed with diethyl ether and dried under reduced pressure to obtain intermediate int_1-4.

LC-MS (ESI): 249 $[M+H]^+$.

Step 4: Synthesis of Compound Int_1-5

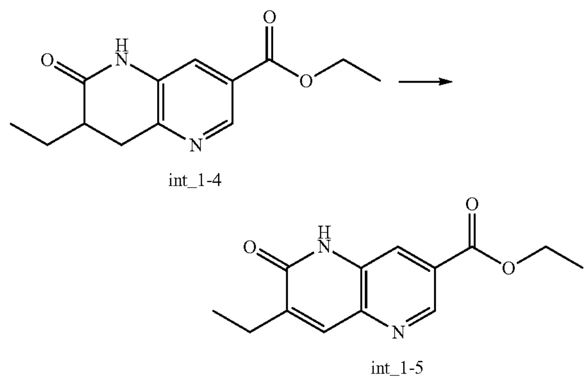

int_1-4 int_1-5

Intermediate int_1-4 (2.00 g, 8.06 mmol) was dissolved in a solution of dioxane (35 mL) at room temperature, 2,3-dichloro-5,6-dicyanobenzoquinone (2.01 g, 8.86 mmol) was added, and the reaction mixture was heated to reflux for 3 h. The reaction mixture was concentrated under reduced pressure to remove the organic solvent, a saturated aqueous sodium bicarbonate solution (50 mL) was added, the mixture was stirred for 1 h and then filtered, and the filter cake was sequentially washed with water and diethyl ether. The filter cake was dried under reduced pressure to obtain intermediate int_1-5.

LC-MS (ESI): 247 $[M+H]^+$.

Step 5: Synthesis of Compound Int 1-6

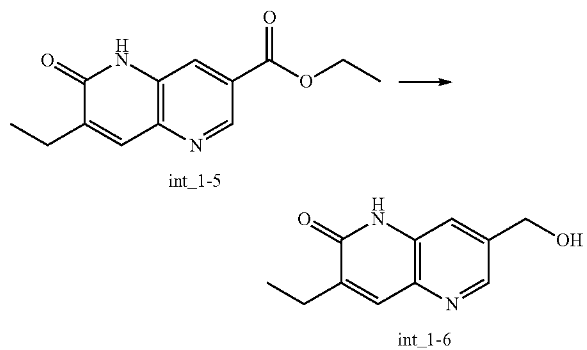

int_1-5 int_1-6

Lithium aluminum hydride (16.24 mL, 16.24 mmol, 1 M in THF) was added to a solution of intermediate int_1-5 (2.00 g, 8.12 mmol) in tetrahydrofuran (40 mL) under nitrogen atmosphere in an ice-water bath, and the reaction mixture was stirred at 0° C. for 1 h. Water (1 mL), 15% sodium hydroxide solution (2 mL) and water (3 mL) were sequentially added to the reaction solution with stirring. After stirring for 15 min, the reaction solution was filtered, and the filtrate was extracted with ethyl acetate (30 mL×4). The organic phases were combined, washed with saturated brine (100 mL), dried over anhydrous sodium sulfate and filtered. The filtrate was concentrated under reduced pressure to remove the organic solvent to obtain a crude product. The crude product was separated and purified by silica gel chromatography to obtain intermediate int_1-6.

LC-MS (ESI): 205 $[M+H]^+$.

Step 6: Synthesis of Compound Int_1-7

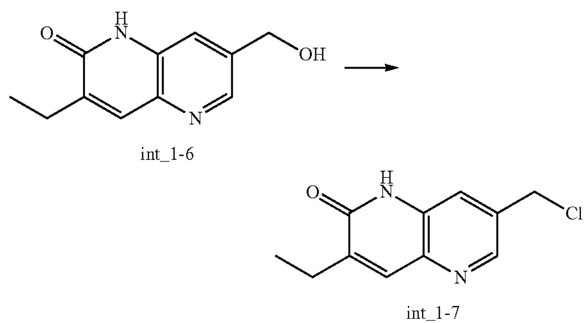

int_1-6 int_1-7

Thionyl chloride (4.26 mL, 58.76 mmol) was added dropwise to a solution of intermediate int 1-6 (2.00 g, 9.79 mmol) and N,N-dimethylformamide (71.58 mg, 0.979 mmol) in dichloromethane with stirring at 0° C. The mixture was stirred at room temperature for 5 h, and the reaction solution was concentrated under reduced pressure to obtain crude intermediate int 1-7, which was directly used in the next step without purification.

Step 7: Synthesis of Compound 1

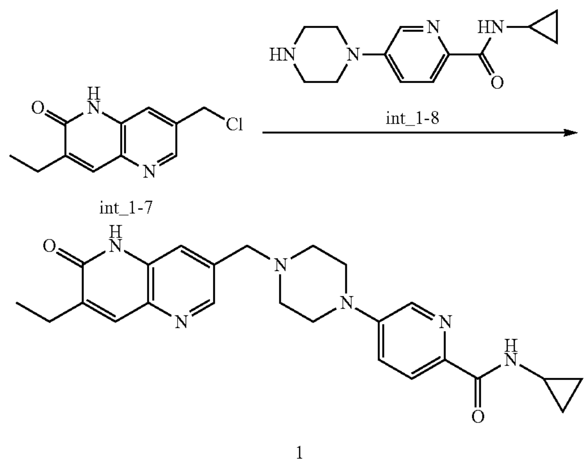

int_1-8 int_1-7

1

Intermediate int_1-7 (crude, 2.00 g), intermediate int_1-8 (2.21 g, 8.98 mmol), potassium iodide (298 mg, 1.80 mmol) and N,N-diisopropylethylamine (5.80 g, 44.91 mmol) were mixed in acetonitrile (25 mL) at room temperature, and the mixture was heated to 80° C. and stirred for 2 h. After the reaction solution was cooled, the organic solvent was removed by concentration under reduced pressure, water (100 mL) was added, and the mixture was basified with a saturated aqueous sodium bicarbonate solution. The mixture was extracted with ethyl acetate (30 mL×4). The organic phases were combined, washed with saturated brine (100 mL), dried over anhydrous sodium sulfate and filtered. The filtrate was concentrated under reduced pressure to remove the organic solvent to obtain a crude product. The crude product was separated and purified by silica gel chromatography to obtain compound 1.

LC-MS (ESI): 433 $[M+H]^+$.

$^1$H NMR (400 MHz, DMSO-$d_6$) δ 11.84 (s, 1H), 8.40 (d, J=1.5 Hz, 1H), 8.33 (d, J=4.9 Hz, 1H), 8.23 (d, J=2.6 Hz, 1H), 7.82 (d, J=8.8 Hz, 1H), 7.75 (s, 1H), 7.62 (s, 1H), 7.48-7.39 (m, 1H), 3.65 (s, 2H), 3.32-3.28 (m, 2H), 2.90-2.79 (m, 1H), 2.59-2.52 (m, 8H), 1.20-1.12 (m, 3H), 0.72-0.56 (m, 4H)

Example 2. Synthesis of Compound 2

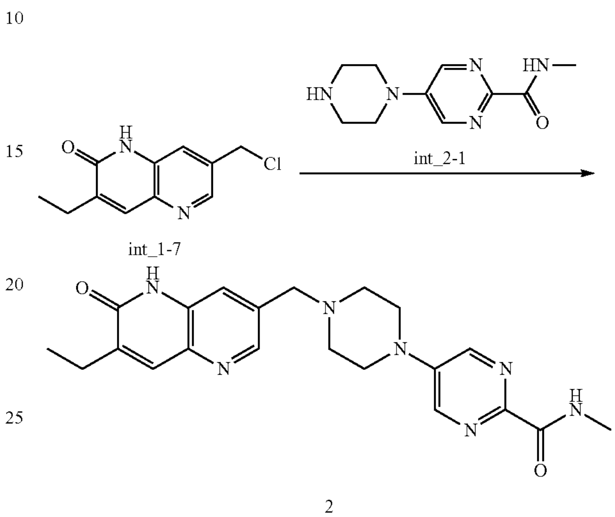

int_2-1 int_1-7

2

Intermediate int_1-7 (2.00 g), intermediate int_2-1 (2.50 g, 11.30 mmol), potassium iodide (298 mg, 1.80 mmol) and N,N-diisopropylethylamine (5.80 g, 44.91 mmol) were mixed in acetonitrile (25 mL) at room temperature, and the mixture was heated to 80° C. and stirred for 2 h. After the reaction solution was cooled, the organic solvent was removed by concentration under reduced pressure, water (100 mL) was added, and the mixture was basified with a saturated aqueous sodium bicarbonate solution. The mixture was extracted with ethyl acetate (30 mL×4). The organic phases were combined, washed with saturated brine (100 mL), dried over anhydrous sodium sulfate and filtered. The filtrate was concentrated under reduced pressure to remove the organic solvent to obtain a crude product. The crude product was separated and purified by silica gel chromatography to obtain compound 2.

LC-MS (ESI): 408 $[M+H]^+$.

Example 3. Synthesis of Compound 3

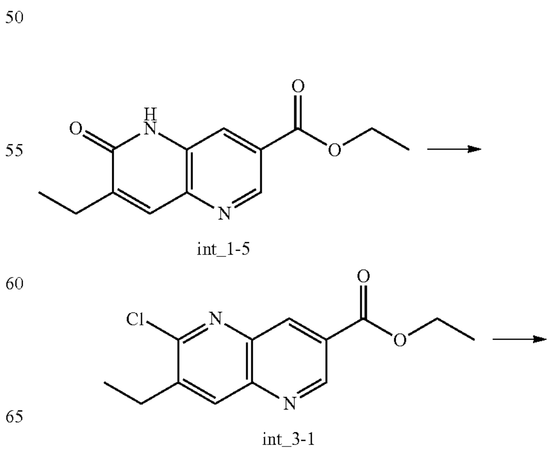

int_1-5 int_3-1

-continued

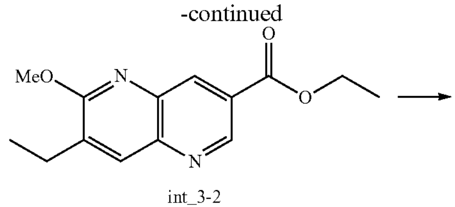

int_3-2

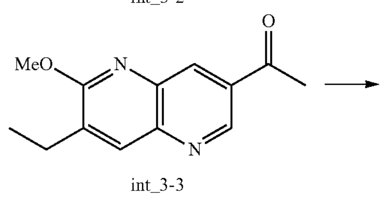

int_3-3

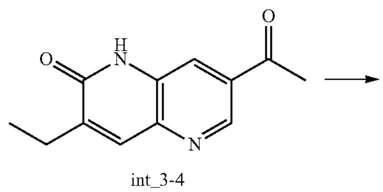

int_3-4

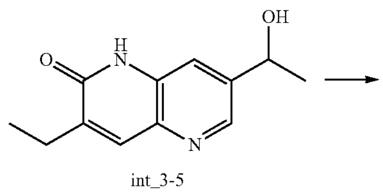

int_3-5

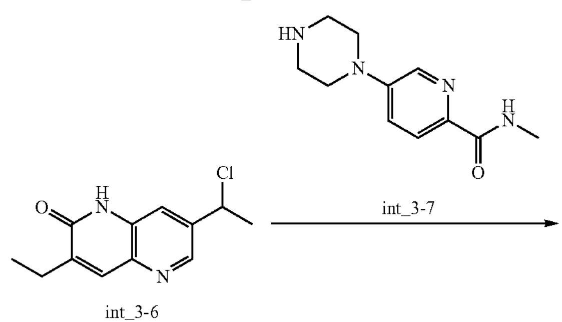

int_3-6

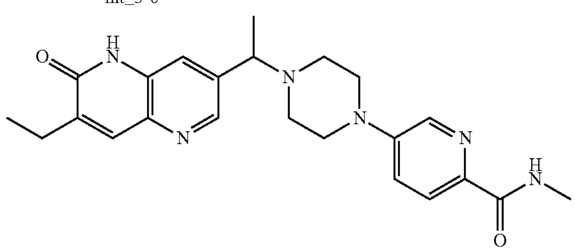

3

Step 1: Synthesis of Compound Int 3-1

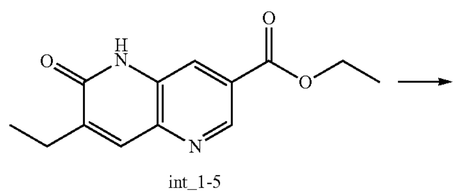

int_1-5

-continued

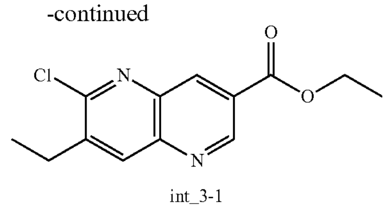

int_3-1

A mixture of intermediate int_1-5 (3.00 g, 12.18 mmol) and phosphorus oxychloride (37.36 g, 243.64 mmol) was heated to 100 °C and stirred for 3 h. After the reaction solution was cooled, phosphorus oxychloride was removed by concentration under reduced pressure, and the residue was poured into water (200 mL) and basified with a saturated aqueous sodium bicarbonate solution. The mixture was extracted with dichloromethane (60 mL×4). The organic phases were combined, washed with saturated brine (100 mL), dried over anhydrous sodium sulfate and filtered. The filtrate was concentrated under reduced pressure to remove the organic solvent to obtain a crude product. The crude product was separated and purified by silica gel chromatography to obtain intermediate int 3-1.

LC-MS (ESI): 265 $[M+H]^+$.

Step 2: Synthesis of Compound Int 3-2

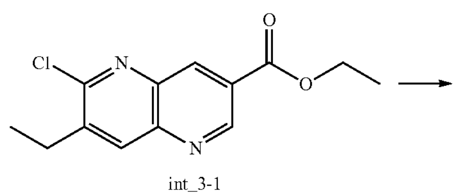

int_3-1

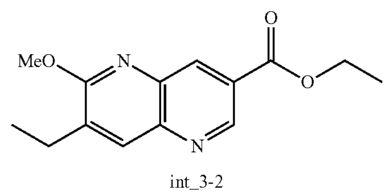

int_3-2

Intermediate int_3-1 (2.00 g, 7.56 mmol) and sodium methoxide (816 mg, 15.11 mmol) were mixed in methylbenzene (30 mL) at room temperature, and the mixture was heated to 50 °C and stirred for 5 h. After being cooled, the reaction solution was poured into water (150 mL) and extracted with ethyl acetate (50 mL×4). The organic phases were combined, washed with saturated brine (100 mL), dried over anhydrous sodium sulfate and filtered. The filtrate was concentrated under reduced pressure to remove the organic solvent to obtain a crude product.

The crude product was separated and purified by silica gel chromatography to obtain intermediate int_3-2.

LC-MS (ESI): 261 $[M+H]^+$.

Step 3: Synthesis of Compound Int_3-3

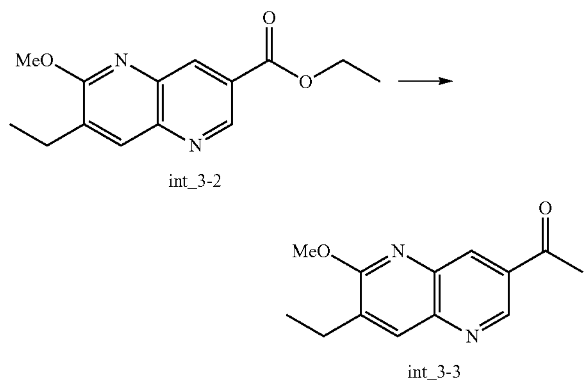

Methyllithium (1.5 M in THF, 7.68 mL, 11.53 mmol) was added to a solution of intermediate int_3-2 (2.00 g, 7.68 mmol) in tetrahydrofuran (30 mL) under nitrogen atmosphere with cooling at −78 °C, and the reaction mixture was stirred at −78 °C for 1 h. The reaction solution was warmed to 0 °C and quenched by dropwise adding a saturated aqueous ammonia chloride solution (20 mL) with stirring, followed by the addition of water (50 mL). The mixture was extracted with ethyl acetate (50 mL×4). The organic phases were combined, washed with saturated brine (50 mL), dried over anhydrous sodium sulfate and filtered. The filtrate was concentrated under reduced pressure to remove the organic solvent to obtain a crude product. The crude product was separated and purified by silica gel chromatography to obtain intermediate int_3-3.

LC-MS (ESI): 231 $[M+H]^+$.

Step 4: Synthesis of Compound Int_3-4

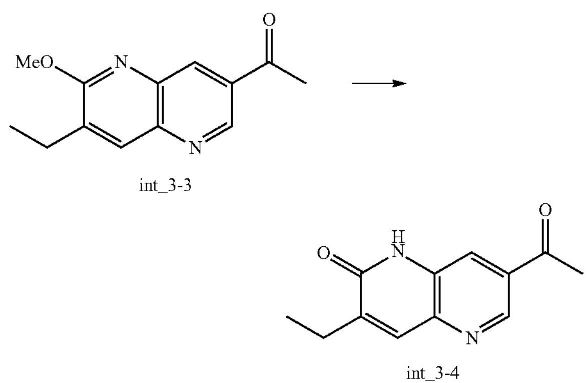

A mixture of intermediate int_3-3 (1.50 g, 6.94 mmol) and 6 N hydrochloric acid (15 mL) was heated to 100° C. and stirred for 2 h. The reaction solution was cooled to 0° C., and basified with 15% aqueous sodium hydroxide solution with stirring to pH=6-7. The mixture was extracted with ethyl acetate (30 mL×3). The organic phases were combined, washed with saturated brine (50 mL), dried over anhydrous sodium sulfate and filtered. The filtrate was concentrated under reduced pressure to remove the organic solvent to obtain intermediate int 3-4.

LC-MS (ESI): 217 $[M+H]^+$.

Step 5: Synthesis of Compound Int_3-5

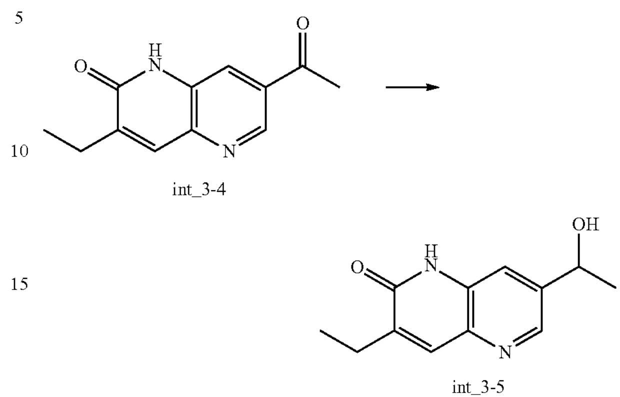

Sodium borohydride (350 mg, 9.25 mmol) was slowly added to a solution of intermediate int_3-4 (1.00 g, 4.62 mmol) in methanol (25 mL) in an ice-water bath, and the reaction mixture was stirred at 0° C. for 0.5 h, then warmed to room temperature and stirred for 2 h. The reaction mixture was concentrated under reduced pressure, water (100 mL) was added, and the mixture was extracted with ethyl acetate (30 mL×3). The organic phases were combined, washed with saturated brine (50 mL), dried over anhydrous sodium sulfate and filtered. The filtrate was concentrated under reduced pressure to remove the organic solvent to obtain a crude product. The crude product was separated and purified by silica gel chromatography to obtain intermediate int_3-5.

LC-MS (ESI): 219 $[M+H]^+$.

Step 6: Synthesis of Compound Int_3-6

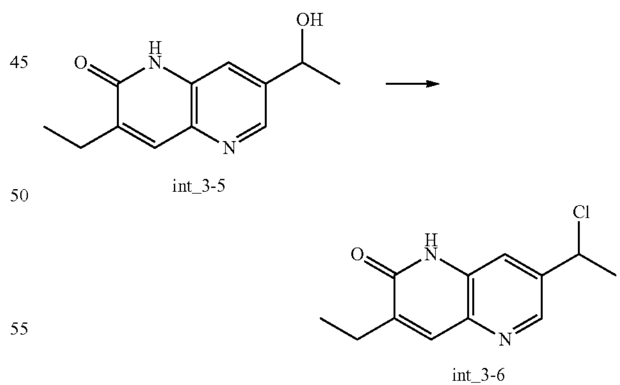

Thionyl chloride (3.27 g, 27.49 mmol) was added dropwise to a solution of intermediate int_3-5 (1.00 g, 4.58 mmol) and N,N-dimethylformamide (33 mg, 0.458 mmol) in dichloromethane (20 mL) with stirring at 0 °C. The mixture was stirred at room temperature for 5 h, and the reaction solution was concentrated under reduced pressure to obtain crude intermediate int_3-6, which was directly used in the next step without purification.

Step 7: Synthesis of Compound 3

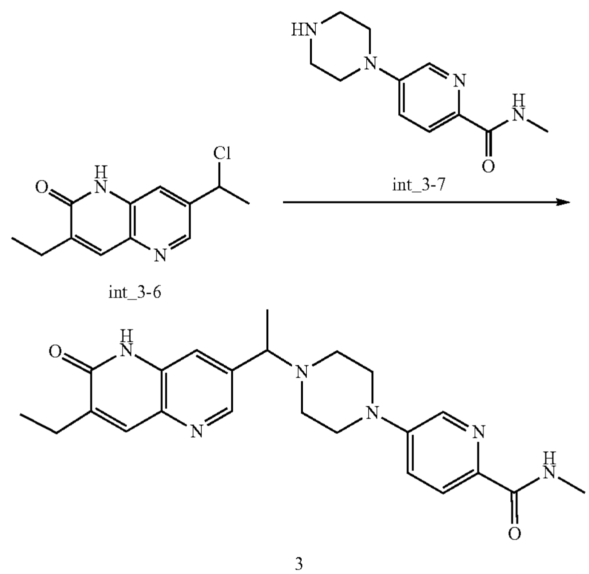

int_3-6

3

Intermediate int_3-6 (1.00 g), intermediate int_3-7 (931 mg, 4.22 mmol), potassium iodide (140 mg, 0.845 mmol) and N,N-diisopropylethylamine (2.73 g, 21.12 mmol) were mixed in acetonitrile (20 mL) at room temperature, and the mixture was heated to 80° C. and stirred for 2 h. After the reaction solution was cooled, the organic solvent was removed by concentration under reduced pressure, water (100 mL) was added, and the mixture was basified with a saturated aqueous sodium bicarbonate solution. The mixture was extracted with ethyl acetate (30 mL×3). The organic phases were combined, washed with saturated brine (100 mL), dried over anhydrous sodium sulfate and filtered. The filtrate was concentrated under reduced pressure to remove the organic solvent to obtain a crude product. The crude product was separated and purified by silica gel chromatography to obtain compound 3.

LC-MS (ESI): 421 $[M+H]^+$.

Example 4. Synthesis of Compound 4

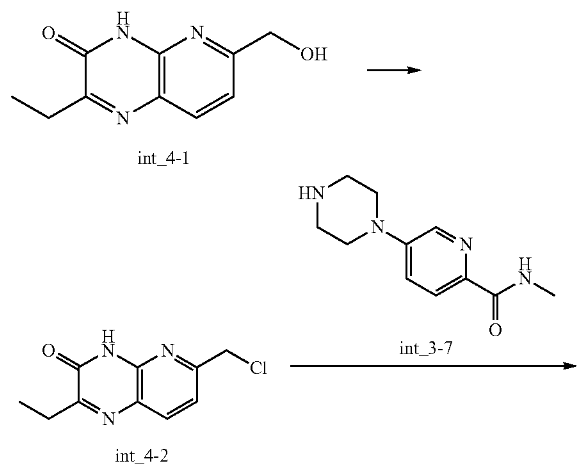

int_4-1 int_4-2

-continued

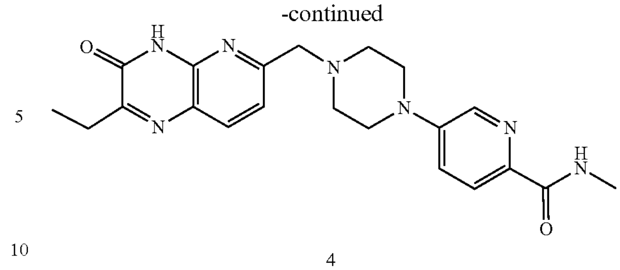

4

Step 1: Synthesis of Compound Int_4-2

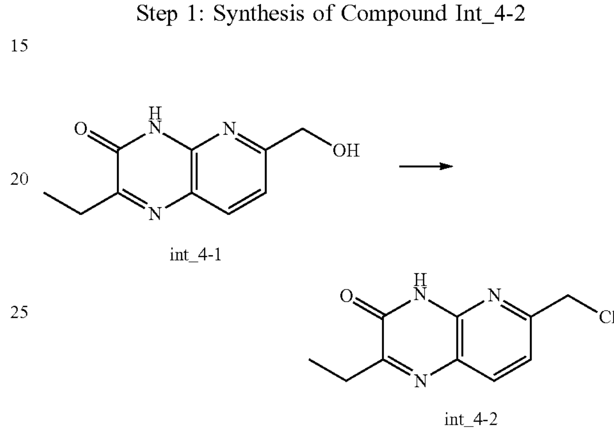

int_4-1 int_4-2

Thionyl chloride (3.48 g, 29.24 mmol) was added dropwise to a solution of intermediate int 4-1 (1.00 g, 4.87 mmol) and N,N-dimethylformamide (36 mg, 0.487 mmol) in dichloromethane (20 mL) with stirring at 0 °C. The mixture was stirred at room temperature for 5 h, and the reaction solution was concentrated under reduced pressure to obtain crude intermediate int 4-2, which was directly used in the next step without purification.

Step 2: Synthesis of Compound 4

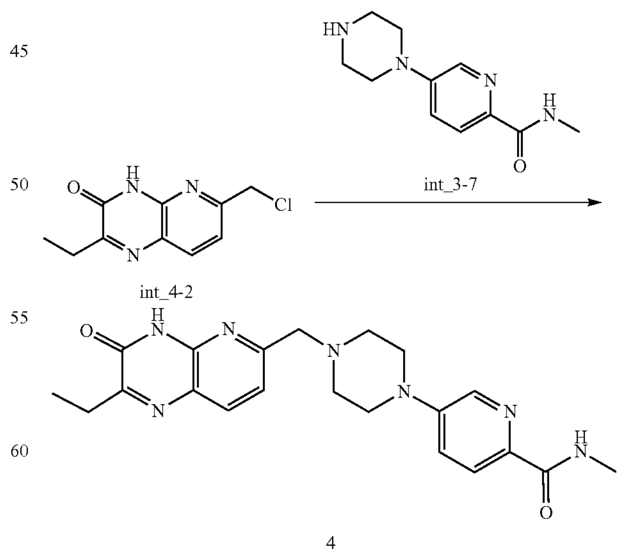

int_4-2

4

Intermediate int_4-2 (1.00 g), intermediate int_3-7 (985 mg, 4.47 mmol), potassium iodide (148 mg, 0.894 mmol)

and N,N-diisopropylethylamine (2.89 g, 22.36 mmol) were mixed in acetonitrile (20 mL) at room temperature, and the mixture was heated to 80 °C and stirred for 2 h. After the reaction solution was cooled, the organic solvent was removed by concentration under reduced pressure, water (100 mL) was added, and the mixture was basified with a saturated aqueous sodium bicarbonate solution. The mixture was extracted with ethyl acetate (30 mL×3). The organic phases were combined, washed with saturated brine (100 mL), dried over anhydrous sodium sulfate and filtered. The filtrate was concentrated under reduced pressure to remove the organic solvent to obtain a crude product. The crude product was separated and purified by silica gel chromatography to obtain compound 4.

LC-MS (ESI): 408 $[M+H]^+$.

Example 5. Synthesis of Compound 5

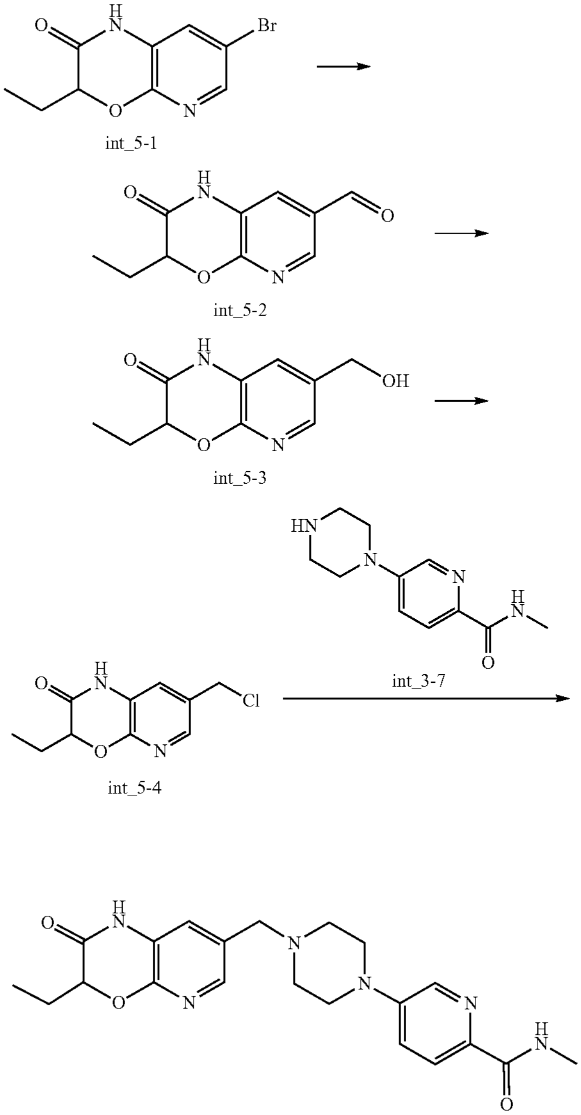

int_5-1 int_5-2 int_5-3 int_3-7 int_5-4

5

Step 1: Synthesis of Compound Int_5-2

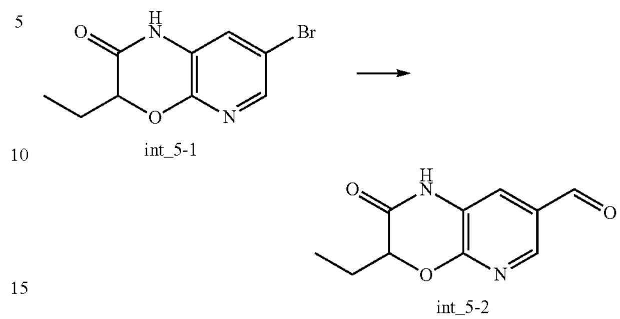

int_5-1 int_5-2

Intermediate int_5-1 (2.00 g, 7.78 mmol), triethylsilane (1.81 g, 15.56 mmol), triethylamine (2.36 g, 23.34 mmol), [1,1'-bis(diphenylphosphino)ferrocene]palladium dichloride dichloromethane complex (635 mg, 0.778 mmol) and anhydrous N,N-dimethylformamide (38 mL) were added to an autoclave at room temperature. After being purged with carbon monoxide, the reaction solution was pressurized to 60 psi with carbon monoxide, heated to 110° C. and stirred for 12 h. After the reaction solution was cooled to room temperature, the pressure was slowly released, the mixture was filtered, and a saturated aqueous sodium bicarbonate solution (200 mL) was added to the filtrate, followed by extraction with dichloromethane (60 mL×3). The organic phases were combined, washed with saturated brine (100 mL×2), dried over anhydrous sodium sulfate and filtered. The filtrate was concentrated under reduced pressure to remove the organic solvent to obtain a crude product. The crude product was separated and purified by silica gel chromatography to obtain intermediate int_5-2.

LC-MS (ESI): 207 $[M+H]^+$.

Step 2: Synthesis of Compound Int 5-3

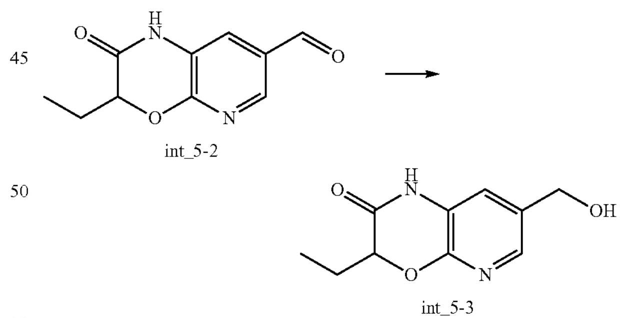

int_5-2 int_5-3

Sodium borohydride (275 mg, 7.27 mmol) was slowly added to a solution of intermediate int 5-2 (1.00 g, 4.85 mmol) in methanol (20 mL) in an ice-water bath, and the reaction mixture was stirred at 0 °C for 0.5 h, then warmed to room temperature and stirred for 2 h. The reaction mixture was concentrated under reduced pressure, water (100 mL) was added, and the mixture was extracted with ethyl acetate (30 mL×3). The organic phases were combined, washed with saturated brine (50 mL), dried over anhydrous sodium sulfate and filtered. The filtrate was concentrated under reduced pressure to remove the organic solvent to obtain a crude product. The crude product was separated and purified by silica gel chromatography to obtain intermediate int_5-3.

LC-MS (ESI): 209 $[M+H]^+$.

Step 3: Synthesis of Compound Int_5-4

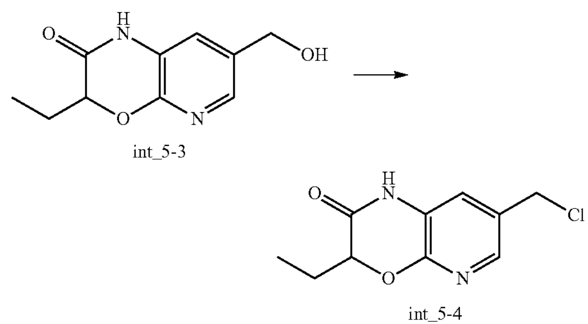

int_5-3 int_5-4

Thionyl chloride (3.43 g, 28.82 mmol) was added dropwise to a solution of intermediate int_5-3 (1.00 g, 4.80 mmol) and N,N-dimethylformamide (35 mg, 0.480 mmol) in dichloromethane (20 mL) with stirring at 0° C. The mixture was stirred at room temperature for 5 h, and the reaction solution was concentrated under reduced pressure to obtain crude intermediate int 5-4, which was directly used in the next step without purification.

Step 4: Synthesis of Compound 5

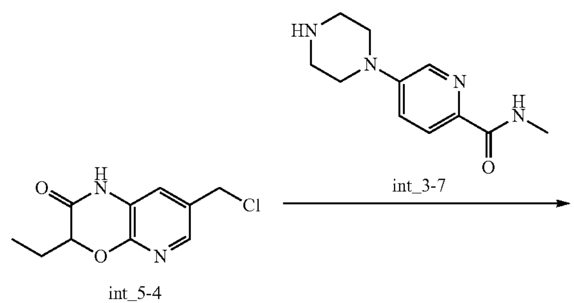

int_5-4

-continued

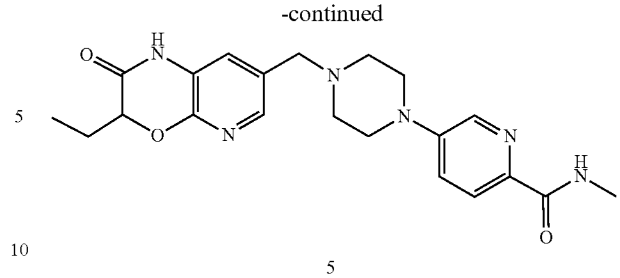

5

Intermediate int_5-4 (1.00 g), intermediate int_3-7 (972 mg, 4.41 mmol), potassium iodide (146 mg, 0.882 mmol) and N,N-diisopropylethylamine (2.85 g, 22.06 mmol) were mixed in acetonitrile (20 mL) at room temperature, and the mixture was heated to 80 °C and stirred for 2 h. After the reaction solution was cooled, the organic solvent was removed by concentration under reduced pressure, water (100 mL) was added, and the mixture was basified with a saturated aqueous sodium bicarbonate solution. The mixture was extracted with ethyl acetate (30 mL×3). The organic phases were combined, washed with saturated brine (100 mL), dried over anhydrous sodium sulfate and filtered. The filtrate was concentrated under reduced pressure to remove the organic solvent to obtain a crude product. The crude product was separated and purified by silica gel chromatography to obtain compound 5.

LC-MS (ESI): 411 $[M+H]^+$.

$^1H$ NMR (400 MHz, $CDCl_3$) δ 9.43 (s, 1H), 8.20-7.95 (m, 2H), 7.82 (s, 2H), 7.15 (d, J=8.8 Hz, 1H), 4.74 (t, J=5.8 Hz, 1H), 3.49 (s, 2H), 3.26 (s, 4H), 3.01 (d, J=5.1 Hz, 3H), 2.58 (s, 4H), 1.91 (s, 2H), 1.13 (t, J=7.4 Hz, 3H)

Examples 6-68. Synthesis of Compounds 6-68

The target compounds 6-68 in Table 1 could be obtained by the synthesis methods of general reaction schemes 1, 2, 3, 4 or 5, or other routes, using different starting materials.

TABLE 1

| Compound | Compound structure | MS $(M + H)^+$ |
|---|---|---|
| 6 | 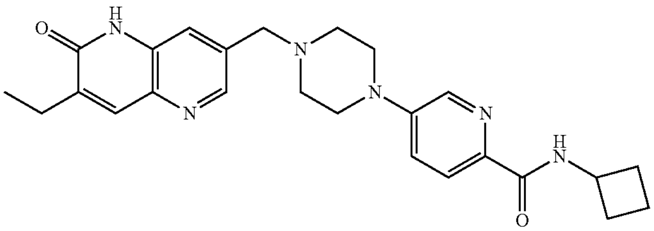 [SMILES: CCc1cc2ncc(CN3CCN(c4ccc(C(=O)NC5CCC5)nc4)CC3)cc2[nH]c1=O] | 447 |

TABLE 1-continued
| Compound | Compound structure | MS (M + H)$^+$ |
|---|---|---|
| 7 | 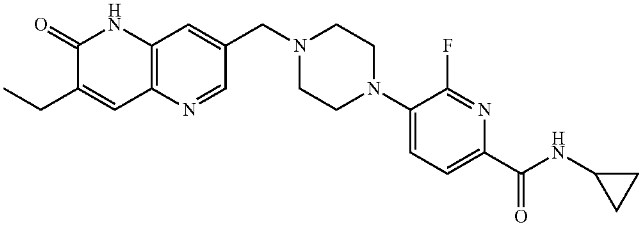 [SMILES: CCc1cc2ncc(CN3CCN(c4ccc(C(=O)NC5CC5)nc4F)CC3)cc2[nH]c1=O] | 451 |
| 8 | 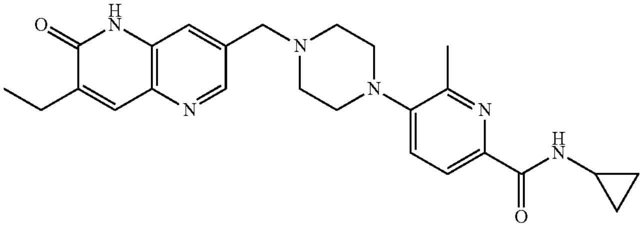 [SMILES: CCc1cc2ncc(CN3CCN(c4ccc(C(=O)NC5CC5)nc4C)CC3)cc2[nH]c1=O] | 447 |
| 9 | 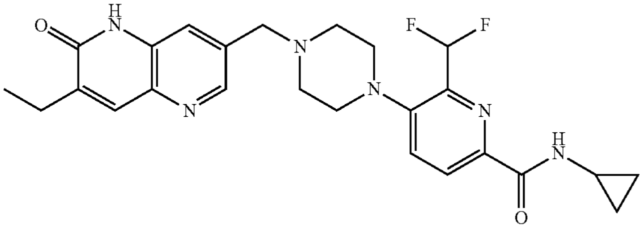 [SMILES: CCc1cc2ncc(CN3CCN(c4ccc(C(=O)NC5CC5)nc4C(F)F)CC3)cc2[nH]c1=O] | 483 |
| 10 | 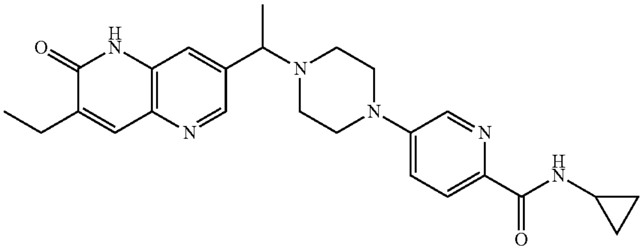 [SMILES: CCc1cc2ncc(C(C)N3CCN(c4ccc(C(=O)NC5CC5)nc4)CC3)cc2[nH]c1=O] | 447 |
| 11 | 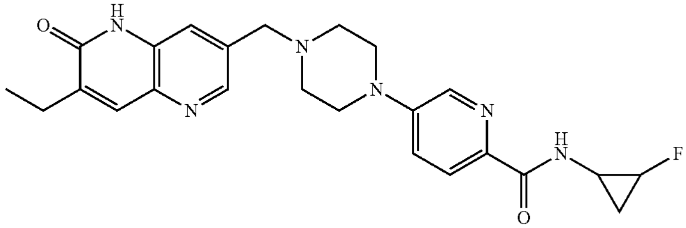 [SMILES: CCc1cc2ncc(CN3CCN(c4ccc(C(=O)NC5CC5F)nc4)CC3)cc2[nH]c1=O] | 451 |
| 12 | 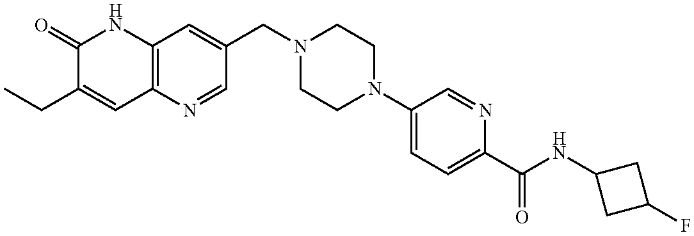 | 465 |

TABLE 1-continued
| Compound | Compound structure | MS $(M + H)^+$ |
|---|---|---|
| 13 | 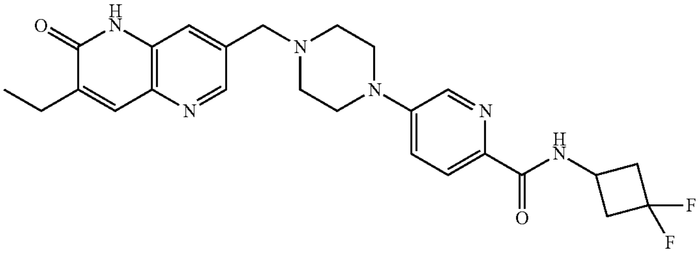 [SMILES: CCc1cc2ncc(CN3CCN(c4ccc(C(=O)NC5CC(F)(F)C5)nc4)CC3)cc2[nH]c1=O] | 483 |
| 14 | 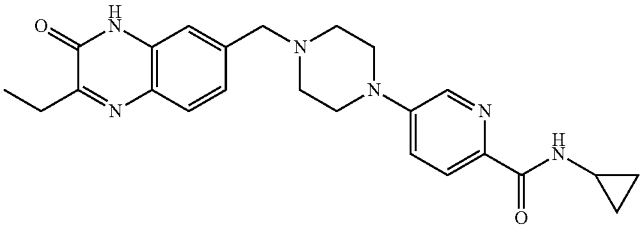 [SMILES: CCc1nc2ccc(CN3CCN(c4ccc(C(=O)NC5CC5)nc4)CC3)cc2[nH]c1=O] | 433 |
| 15 | 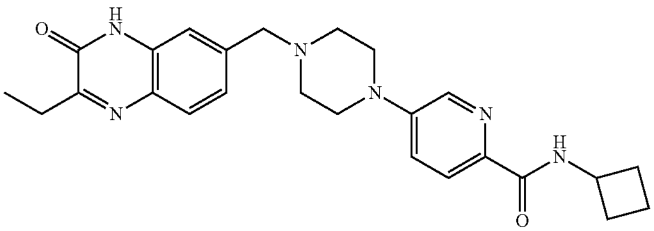 [SMILES: CCc1nc2ccc(CN3CCN(c4ccc(C(=O)NC5CCC5)nc4)CC3)cc2[nH]c1=O] | 447 |
| 16 | 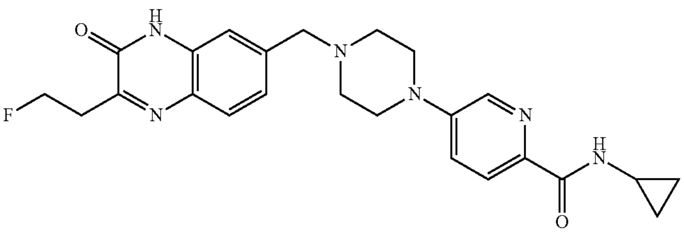 [SMILES: O=C(NC1CC1)c1ccc(N2CCN(Cc3ccc4nc(CCF)c(=O)[nH]c4c3)CC2)cn1] | 451 |
| 17 | 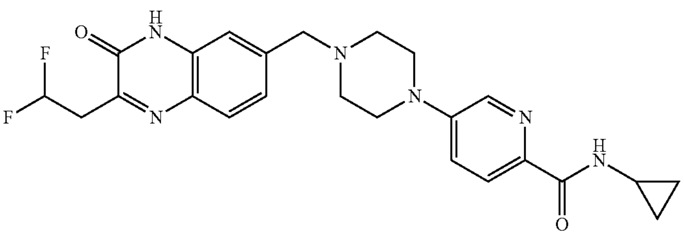 [SMILES: O=C(NC1CC1)c1ccc(N2CCN(Cc3ccc4nc(CC(F)F)c(=O)[nH]c4c3)CC2)cn1] | 469 |
| 18 | 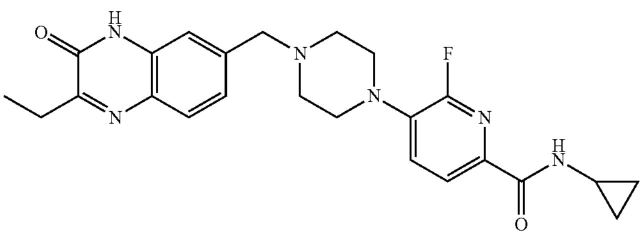 [SMILES: CCc1nc2ccc(CN3CCN(c4ccc(C(=O)NC5CC5)nc4F)CC3)cc2[nH]c1=O] | 451 |

TABLE 1-continued
| Compound | Compound structure | MS (M + H)$^+$ |
|---|---|---|
| 19 | 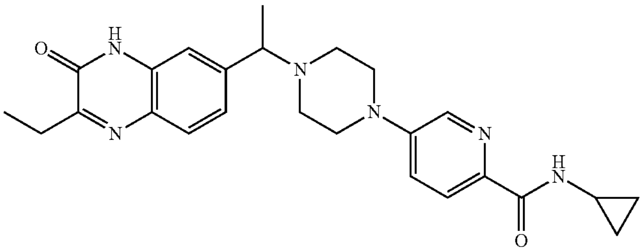 [SMILES: CCc1nc2ccc(C(C)N3CCN(c4ccc(C(=O)NC5CC5)nc4)CC3)cc2[nH]c1=O] | 447 |
| 20 | 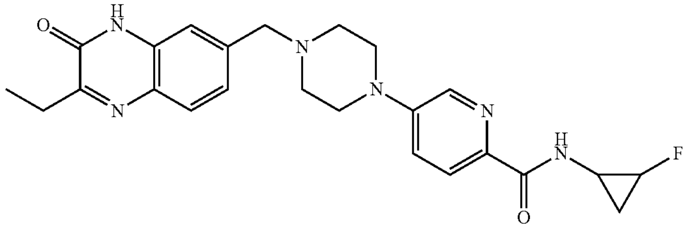 [SMILES: CCc1nc2ccc(CN3CCN(c4ccc(C(=O)NC5CC5F)nc4)CC3)cc2[nH]c1=O] | 451 |
| 21 | 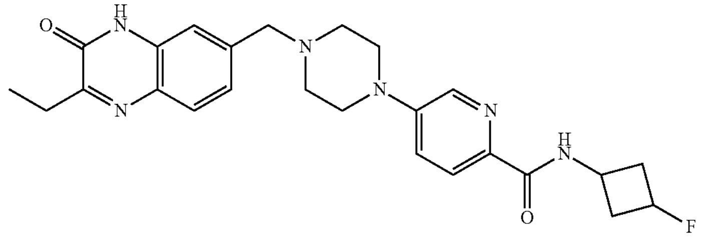 [SMILES: CCc1nc2ccc(CN3CCN(c4ccc(C(=O)NC5CC(F)C5)nc4)CC3)cc2[nH]c1=O] | 465 |
| 22 | 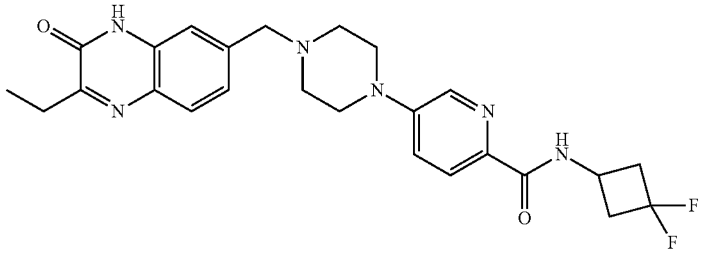 [SMILES: CCc1nc2ccc(CN3CCN(c4ccc(C(=O)NC5CC(F)(F)C5)nc4)CC3)cc2[nH]c1=O] | 483 |
| 23 | 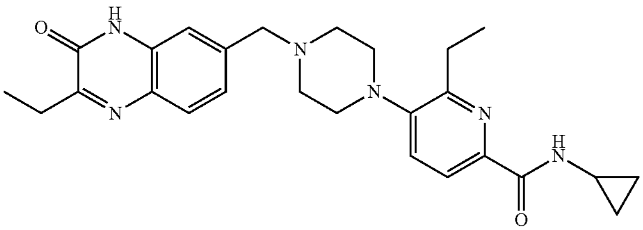 [SMILES: CCc1nc(C(=O)NC2CC2)ccc1N1CCN(Cc2ccc3nc(CC)c(=O)[nH]c3c2)CC1] | 461 |
| 24 | 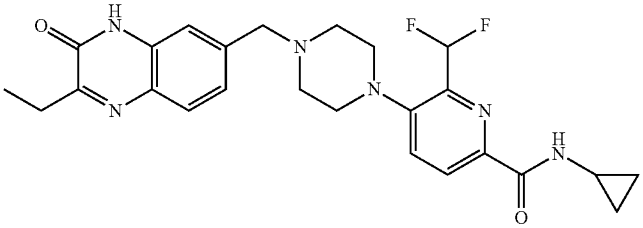 [SMILES: CCc1nc2ccc(CN3CCN(c4ccc(C(=O)NC5CC5)nc4C(F)F)CC3)cc2[nH]c1=O] | 483 |

TABLE 1-continued
| Compound | Compound structure | MS (M + H)+ |
|---|---|---|
| 25 | 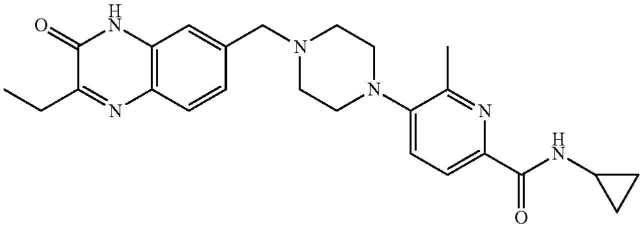 [SMILES: CCc1nc2ccc(CN3CCN(c4ccc(C(=O)NC5CC5)nc4C)CC3)cc2[nH]c1=O] | 447 |
| 26 | 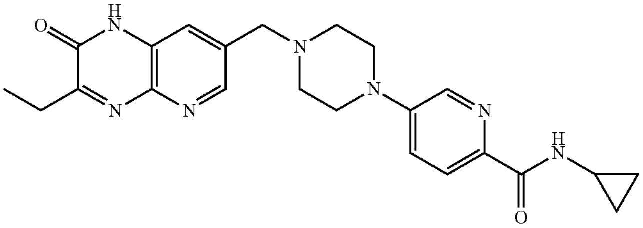 [SMILES: CCc1nc2ncc(CN3CCN(c4ccc(C(=O)NC5CC5)nc4)CC3)cc2[nH]c1=O] | 434 |
| 27 | 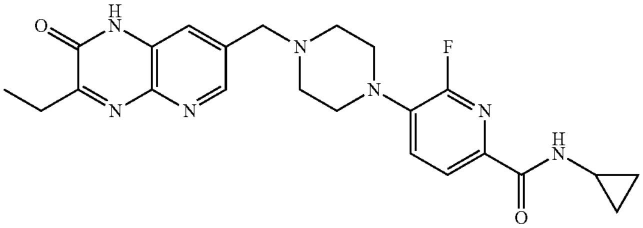 [SMILES: CCc1nc2ncc(CN3CCN(c4ccc(C(=O)NC5CC5)nc4F)CC3)cc2[nH]c1=O] | 452 |
| 28 | 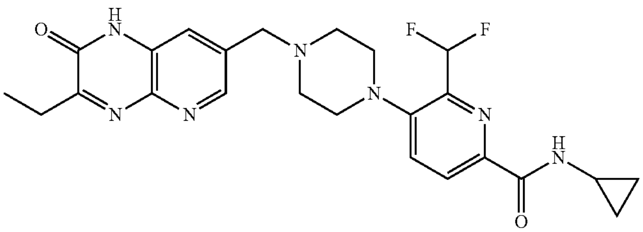 [SMILES: CCc1nc2ncc(CN3CCN(c4ccc(C(=O)NC5CC5)nc4C(F)F)CC3)cc2[nH]c1=O] | 484 |
| 29 | 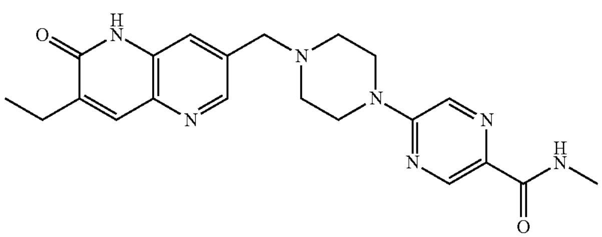 [SMILES: CCc1cc2ncc(CN3CCN(c4cnc(C(=O)NC)cn4)CC3)cc2[nH]c1=O] | 408 |
| 30 | 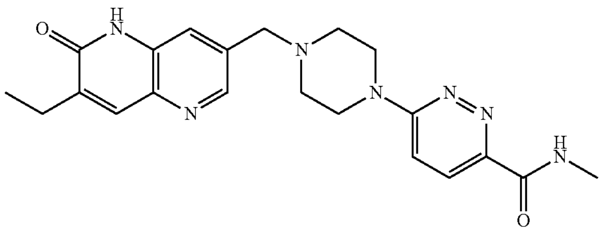 [SMILES: CCc1cc2ncc(CN3CCN(c4ccc(C(=O)NC)nn4)CC3)cc2[nH]c1=O] | 408 |

TABLE 1-continued
| Compound | Compound structure | MS (M + H)+ |
| --- | --- | --- |
| 31 | 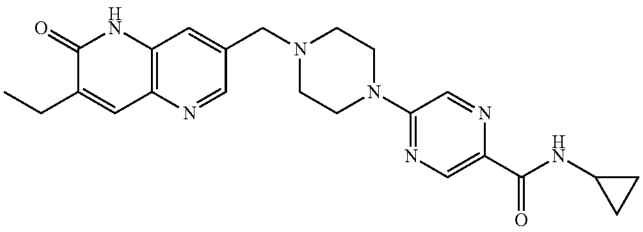 [SMILES: CCc1cc2ncc(CN3CCN(c4cnc(C(=O)NC5CC5)cn4)CC3)cc2[nH]c1=O] | 434 |
| 32 | 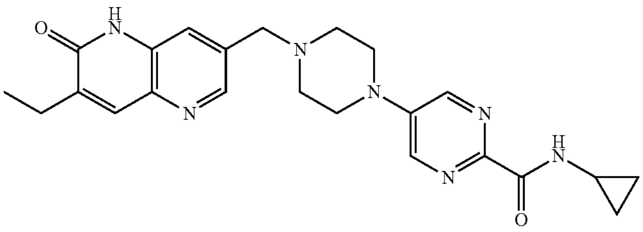 [SMILES: CCc1cc2ncc(CN3CCN(c4cnc(C(=O)NC5CC5)nc4)CC3)cc2[nH]c1=O] | 434 |
| 33 | 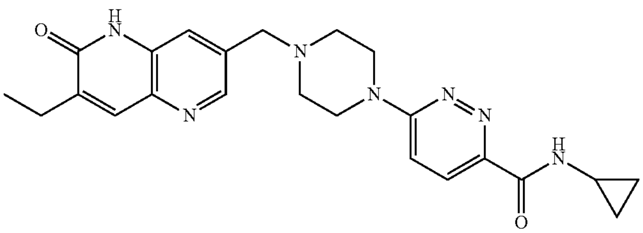 [SMILES: CCc1cc2ncc(CN3CCN(c4ccc(C(=O)NC5CC5)nn4)CC3)cc2[nH]c1=O] | 434 |
| 34 | 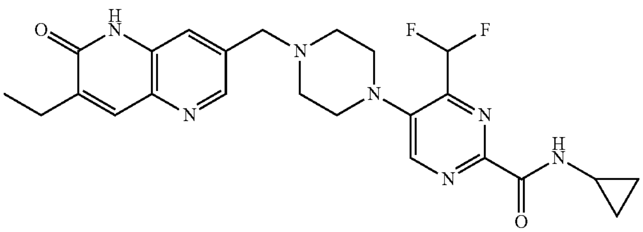 [SMILES: CCc1cc2ncc(CN3CCN(c4cnc(C(=O)NC5CC5)nc4C(F)F)CC3)cc2[nH]c1=O] | 484 |
| 35 | 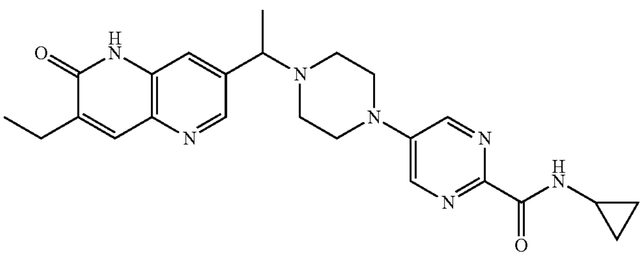 [SMILES: CCc1cc2ncc(C(C)N3CCN(c4cnc(C(=O)NC5CC5)nc4)CC3)cc2[nH]c1=O] | 448 |
| 36 | 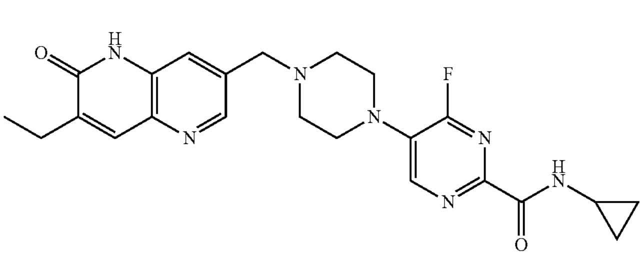 [SMILES: CCc1cc2ncc(CN3CCN(c4cnc(C(=O)NC5CC5)nc4F)CC3)cc2[nH]c1=O] | 452 |

TABLE 1-continued
| Compound | Compound structure | MS (M + H)$^+$ |
| --- | --- | --- |
| 37 | 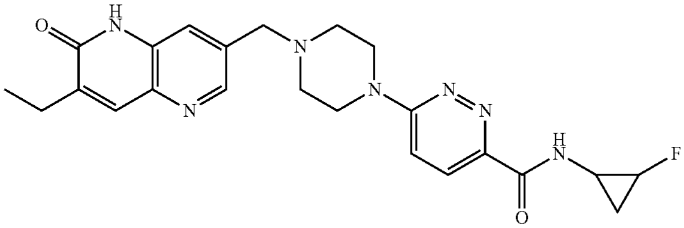 [SMILES: CCc1cc2ncc(CN3CCN(c4ccc(C(=O)NC5CC5F)nn4)CC3)cc2[nH]c1=O] | 452 |
| 38 | 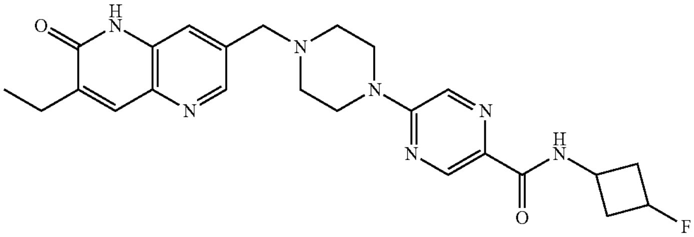 [SMILES: CCc1cc2ncc(CN3CCN(c4cnc(C(=O)NC5CC(F)C5)cn4)CC3)cc2[nH]c1=O] | 466 |
| 39 | 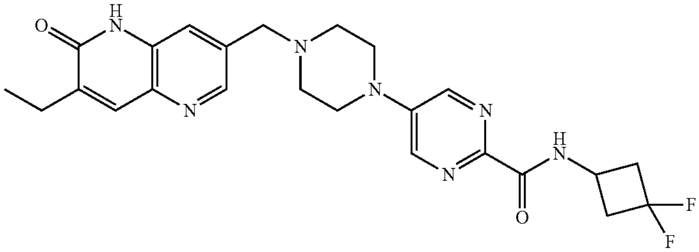 [SMILES: CCc1cc2ncc(CN3CCN(c4cnc(C(=O)NC5CC(F)(F)C5)nc4)CC3)cc2[nH]c1=O] | 484 |
| 40 | 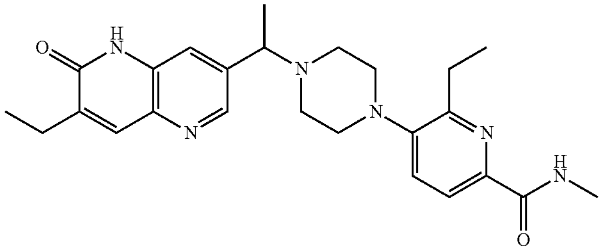 [SMILES: CCc1nc(C(=O)NC)ccc1N1CCN(C(C)c2cnc3cc(CC)c(=O)[nH]c3c2)CC1] | 449 |
| 41 | 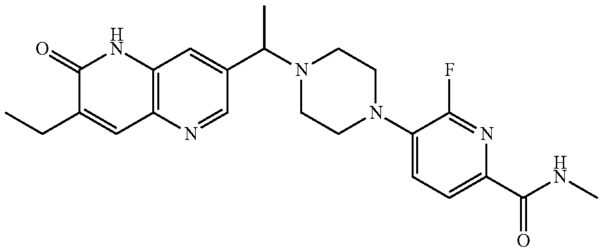 [SMILES: CCc1cc2ncc(C(C)N3CCN(c4ccc(C(=O)NC)nc4F)CC3)cc2[nH]c1=O] | 439 |
| 42 | 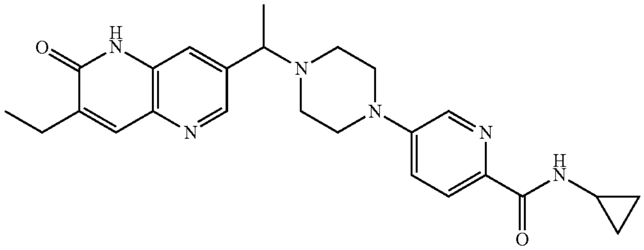 [SMILES: CCc1cc2ncc(C(C)N3CCN(c4ccc(C(=O)NC5CC5)nc4)CC3)cc2[nH]c1=O] | 447 |

TABLE 1-continued
| Compound | Compound structure | MS $(M + H)^+$ |
| --- | --- | --- |
| 43 | 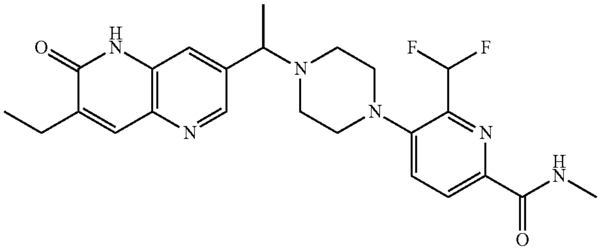 [SMILES: CCc1cc2ncc(C(C)N3CCN(c4ccc(C(=O)NC)nc4C(F)F)CC3)cc2[nH]c1=O] | 471 |
| 44 | 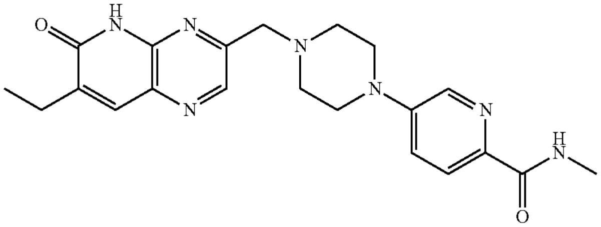 [SMILES: CCc1cc2ncc(CN3CCN(c4ccc(C(=O)NC)nc4)CC3)nc2[nH]c1=O] | 408 |
| 45 | 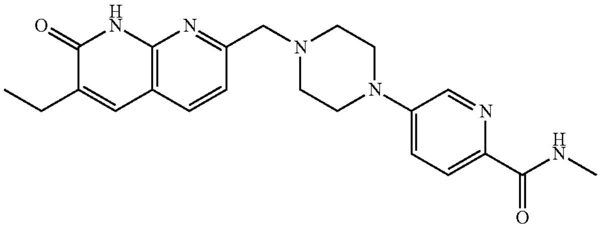 | 407 |
| 46 | 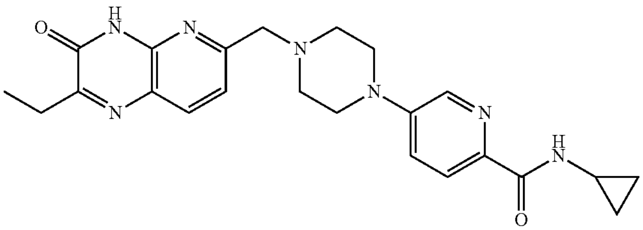 [SMILES: CCc1nc2ccc(CN3CCN(c4ccc(C(=O)NC5CC5)nc4)CC3)nc2[nH]c1=O] | 434 |
| 47 | 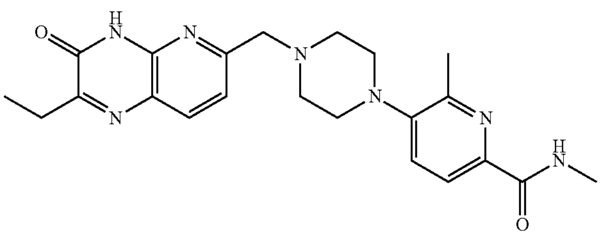 [SMILES: CCc1nc2ccc(CN3CCN(c4ccc(C(=O)NC)nc4C)CC3)nc2[nH]c1=O] | 422 |
| 48 | 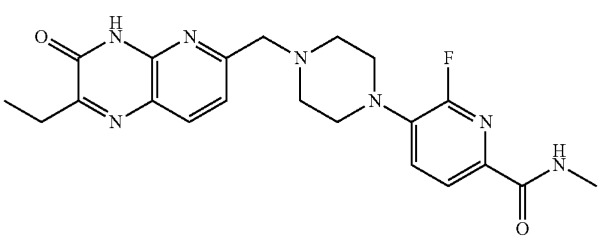 [SMILES: CCc1nc2ccc(CN3CCN(c4ccc(C(=O)NC)nc4F)CC3)nc2[nH]c1=O] | 426 |

TABLE 1-continued
| Compound | Compound structure | MS (M + H)+ |
|---|---|---|
| 49 | 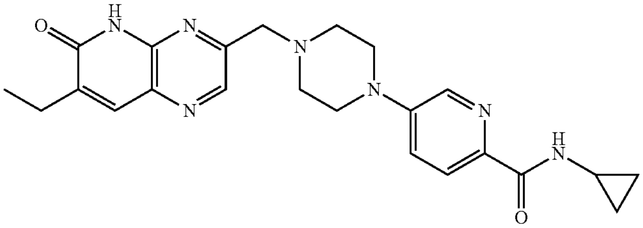 | 434 |
| 50 | 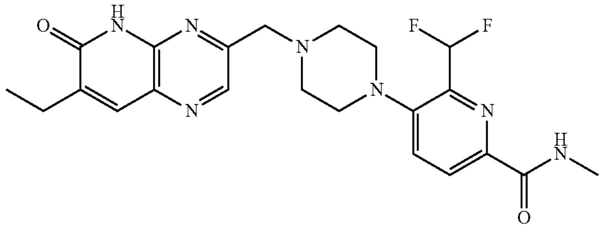 [SMILES: CCc1cc2ncc(CN3CCN(c4ccc(C(=O)NC)nc4C(F)F)CC3)nc2[nH]c1=O] | 458 |
| 51 | 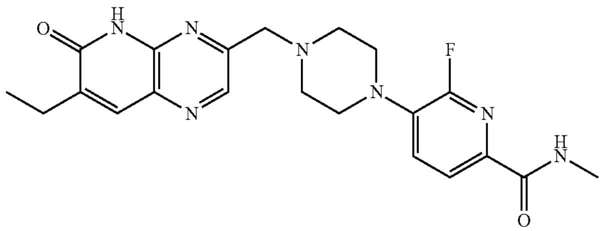 [SMILES: CCc1cc2ncc(CN3CCN(c4ccc(C(=O)NC)nc4F)CC3)nc2[nH]c1=O] | 426 |
| 52 | 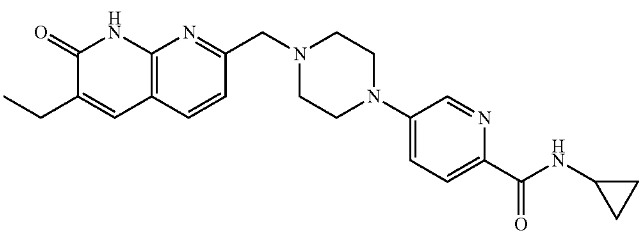 [SMILES: CCc1cc2ccc(CN3CCN(c4ccc(C(=O)NC5CC5)nc4)CC3)nc2[nH]c1=O] | 433 |
| 53 | 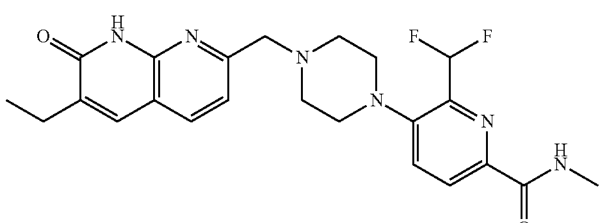 | 457 |
| 54 | 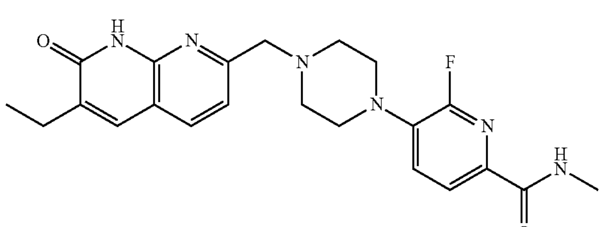 | 425 |

TABLE 1-continued
| Compound | Compound structure | MS $(M + H)^+$ |
|---|---|---|
| 55 | 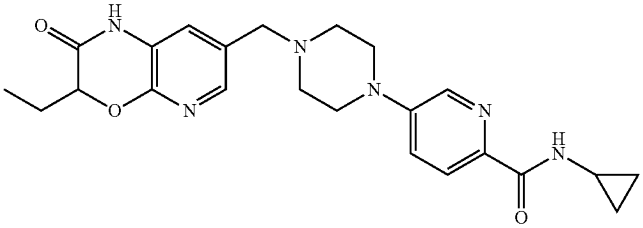 [SMILES: CCC1Oc2ncc(CN3CCN(c4ccc(C(=O)NC5CC5)nc4)CC3)cc2NC1=O] | 437 |
| 56 | 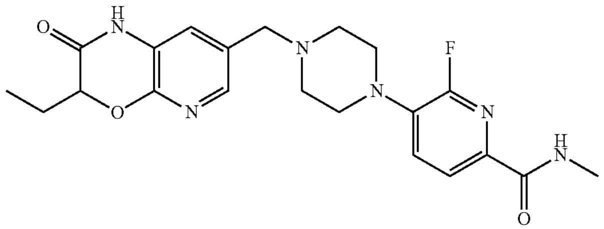 [SMILES: CCC1Oc2ncc(CN3CCN(c4ccc(C(=O)NC)nc4F)CC3)cc2NC1=O] | 429 |
| 57 | 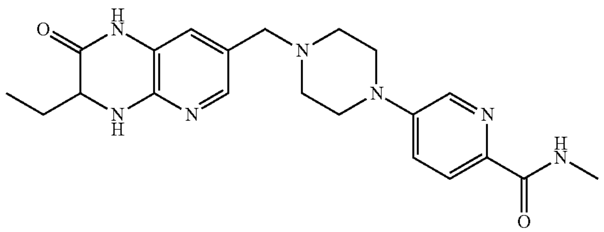 [SMILES: CCC1Nc2ncc(CN3CCN(c4ccc(C(=O)NC)nc4)CC3)cc2NC1=O] | 410 |
| 58 | 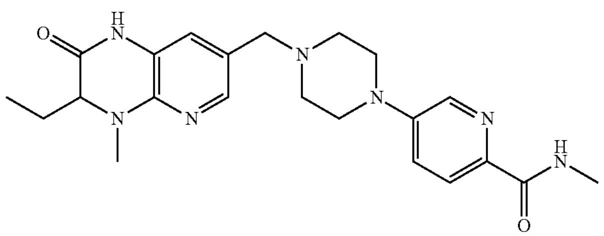 [SMILES: CCC1C(=O)Nc2cc(CN3CCN(c4ccc(C(=O)NC)nc4)CC3)cnc2N1C] | 424 |
| 59 | 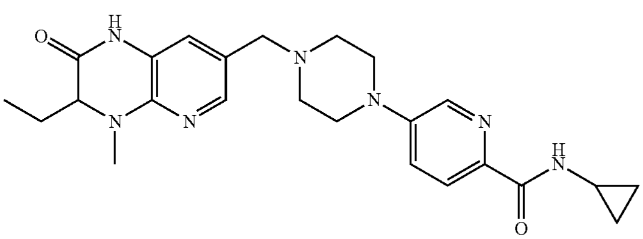 | 450 |
| 60 | 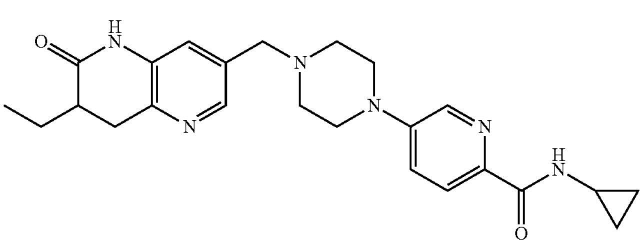 [SMILES: CCC1Cc2ncc(CN3CCN(c4ccc(C(=O)NC5CC5)nc4)CC3)cc2NC1=O] | 435 |

TABLE 1-continued
| Compound | Compound structure | MS (M + H)+ |
| --- | --- | --- |
| 61 | 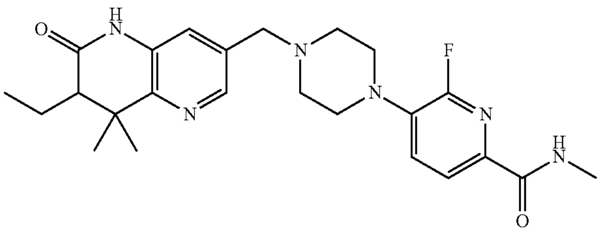 [SMILES: CCC1C(=O)Nc2cc(CN3CCN(c4ccc(C(=O)NC)nc4F)CC3)cnc2C1(C)C] | 455 |
| 62 | 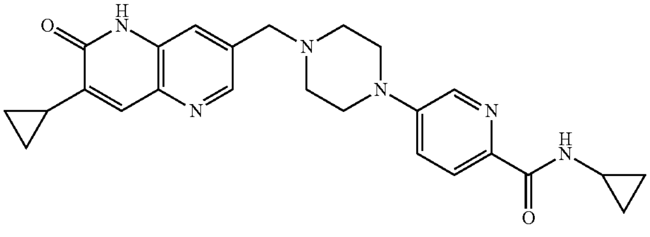 [SMILES: O=C(NC1CC1)c1ccc(N2CCN(Cc3cnc4cc(C5CC5)c(=O)[nH]c4c3)CC2)cn1] | 445 |
| 63 | 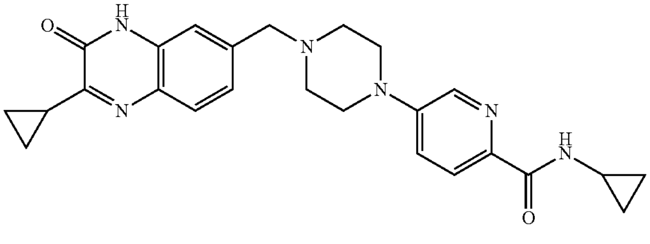 [SMILES: O=C(NC1CC1)c1ccc(N2CCN(Cc3ccc4nc(C5CC5)c(=O)[nH]c4c3)CC2)cn1] | 445 |
| 64 | 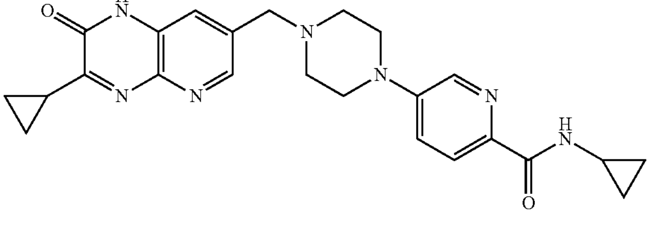 | 446 |
| 65 | 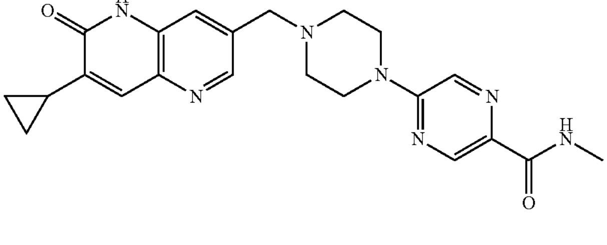 | 420 |
| 66 | 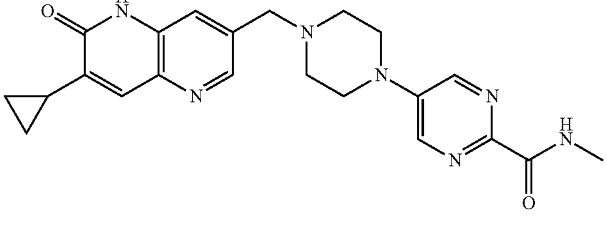 | 420 |

TABLE 1-continued

| Compound | Compound structure | MS $(M + H)^+$ |
|---|---|---|
| 67 | 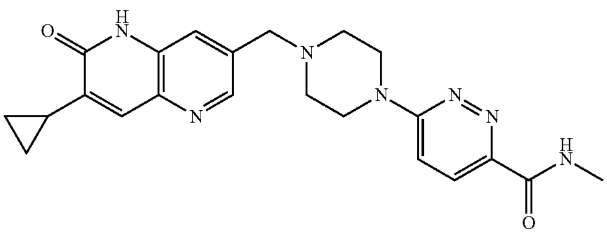 [SMILES: CNC(=O)c1ccc(N2CCN(Cc3cnc4cc(C5CC5)c(=O)[nH]c4c3)CC2)nn1] | 420 |
| 68 | 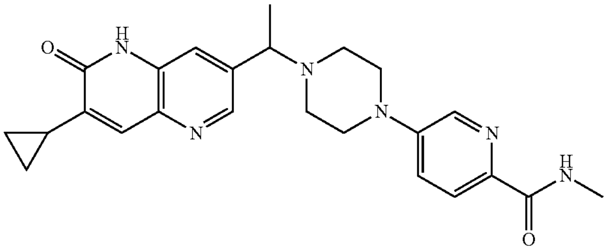 [SMILES: CNC(=O)c1ccc(N2CCN(C(C)c3cnc4cc(C5CC5)c(=O)[nH]c4c3)CC2)cn1] | 433 |

Example 69. Experiment on In Vitro Inhibition of Activity of Poly (ADP-Ribose) Polymerase [PARP-1 Enzyme] with Compounds of the Present Invention The histones were coated onto 384-well plates at 4 °C overnight, rinsed three times with a PBST buffer, and blocked at room temperature for 1 h. After 1 h, the histones were rinsed three more times with PBST, DMSO or a serially diluted compound, and a mixture containing PARP-1 enzymes and DNA was added, and the resulting mixture was incubated at 25 °C for 10 min. After 10 min $NAD^+$ was added to start the reaction. After reacting at room temperature for 60 min, the reaction solution was rinsed three times with PBST, and the level of poly/mono-ADP ribose on the histones was detected by the addition of a poly/mono-ADP ribose antibody conjugated with horseradish peroxidase (MIP). After incubation at room temperature for 1 h, HRP substrates ECL A and B were added, and Envision quantified chemiluminescence. The inhibition percentages and $IC_{50}$ of the compounds were calculated compared to the control group DMSO. The results are shown in Table 2 below.

TABLE 2

| Inhibitory activity of the compounds of the present invention against PARP-1 ($IC_{50}$, nM) | |
|---|---|
| Compound | $IC_{50}$ |
| 1 | 0.54 nM |
| 2 | +++ |
| 3 | +++ |
| 4 | +++ |
| 5 | 1.7 nM |
| 6 | + |
| 7 | ++ |
| 8 | ++ |
| 9 | ++ |
| 10 | ++ |
| 11 | +++ |
| 13 | +++ |
| 14 | +++ |

TABLE 2-continued

| Inhibitory activity of the compounds of the present invention against PARP-1 ($IC_{50}$, nM) | |
|---|---|
| Compound | $IC_{50}$ |
| 15 | +++ |
| 16 | +++ |
| 17 | +++ |
| 18 | +++ |
| 19 | +++ |
| 20 | +++ |
| 21 | +++ |
| 22 | +++ |
| 23 | +++ |
| 24 | +++ |
| 25 | +++ |
| 26 | +++ |
| 27 | ++ |
| 28 | ++ |
| 29 | ++ |
| 30 | ++ |
| 31 | ++ |
| 32 | ++ |
| 33 | +++ |
| 34 | +++ |
| 35 | +++ |
| 36 | +++ |
| 37 | ++ |
| 38 | ++ |
| 39 | ++ |
| 40 | ++ |
| 41 | ++ |
| 42 | ++ |
| 43 | +++ |
| 44 | +++ |
| 45 | +++ |
| 46 | +++ |
| 47 | +++ |
| 48 | +++ |
| 49 | +++ |
| 50 | +++ |
| 51 | ++ |
| 52 | ++ |
| 53 | ++ |
| 54 | +++ |
| 55 | ++ |
| 56 | +++ |
| 57 | +++ |

TABLE 2-continued

| Inhibitory activity of the compounds of the present invention against PARP-1 ($IC_{50}$, nM) | |
|---|---|
| Compound | $IC_{50}$ |
| 58 | +++ |
| 59 | ++ |
| 60 | ++ |
| 61 | +++ |
| 62 | ++ |
| 63 | +++ |
| 64 | +++ |
| 65 | ++ |
| 66 | ++ |
| 67 | +++ |
| 68 | +++ |

+++ means that $IC_{50}$ is less than or equal to 10 nM
++ means that $IC_{50}$ is 10 nM to 50 nM
+ means that $IC_{50}$ is greater than 50 nM.

As can be seen from the data in Table 2, the compounds of the present invention have good inhibitory activities against PARP-1.

Although specific embodiments of the present invention have been described above, it will be appreciated by those skilled in the art that these embodiments are merely illustrative and that many changes or modifications can be made to these embodiments without departing from the principles and spirit of the present invention. The protection scope of the present invention is therefore defined by the appended claims.

The invention claimed is:

1. A compound of general formula (1), or an optical isomer, a crystalline form, a pharmaceutically acceptable salt, a hydrate, or a solvate thereof:

(1)

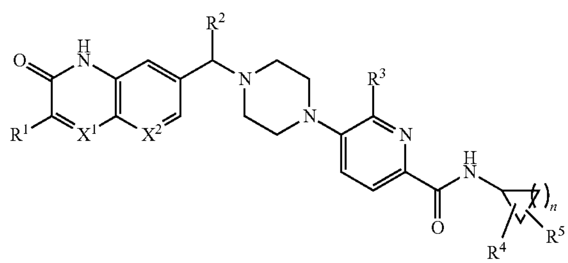

wherein in general formula (1):

$R^1$ is (C1-C4) alkyl, (C1-C4) fluoroalkyl, or (C3-C5) cycloalkyl;

$R^2$ is H or (C1-C3) alkyl;

$R^3$ is H, F, Cl, (C1-C4) alkyl, or (C1-C4) fluoroalkyl;

n is 1 or 2;

$R^4$ and $R^5$ represent two substituents on a cycloalkyl ring, and are each independently H or F; and $X^1$ and $X^2$ are each independently CH or N.

2. The compound, or the optical isomer, the crystalline form, the pharmaceutically acceptable salt, the hydrate, or the solvate thereof according to claim 1, wherein the compound has one of the following structures:

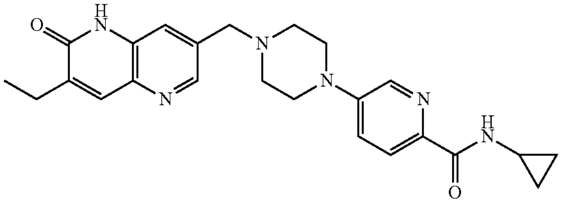

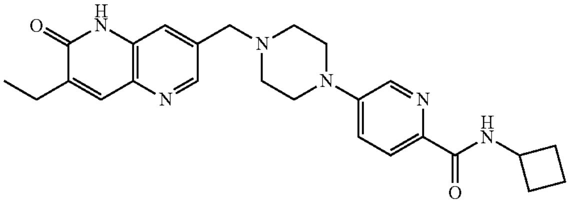

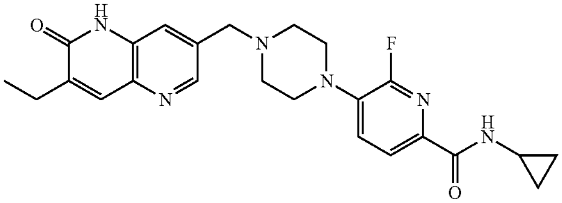

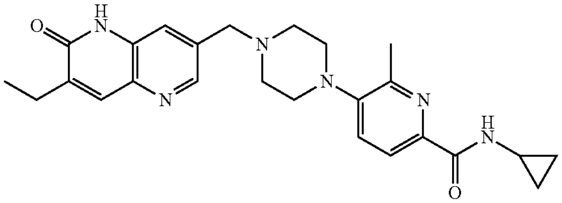

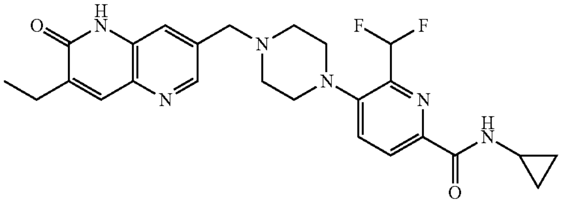

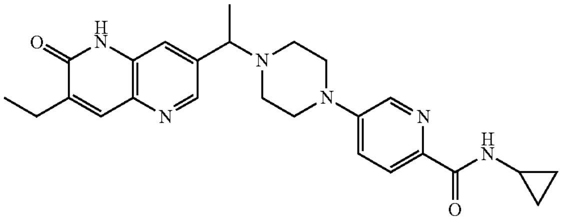

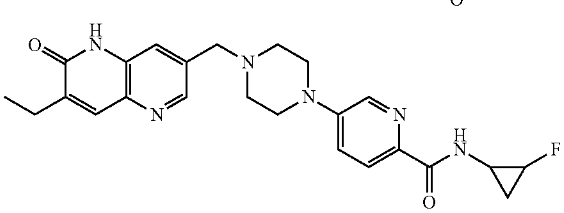

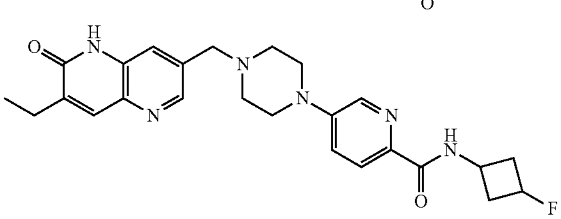

-continued
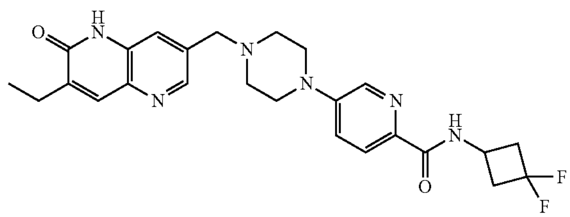
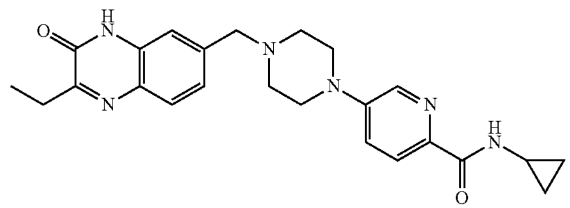
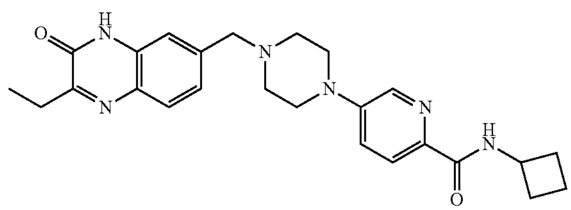
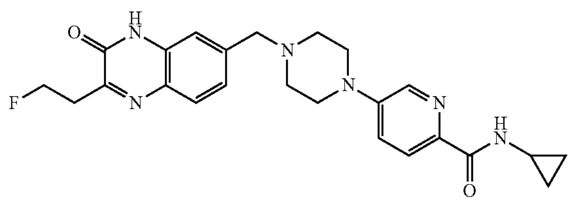
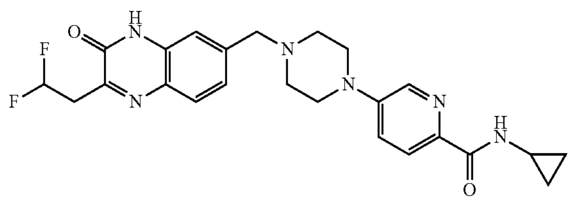
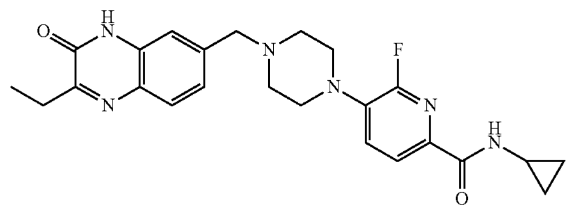
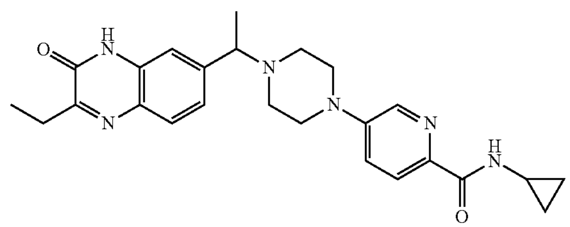
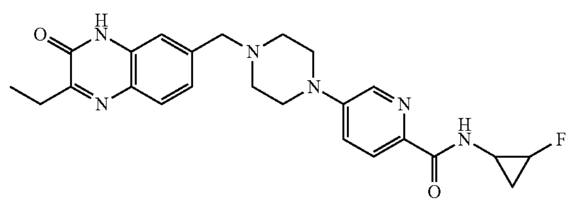
-continued
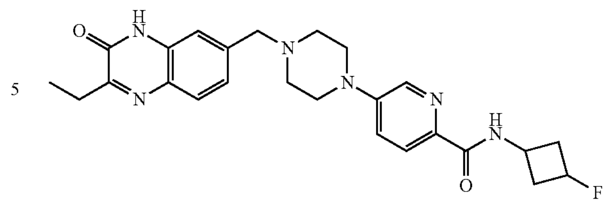
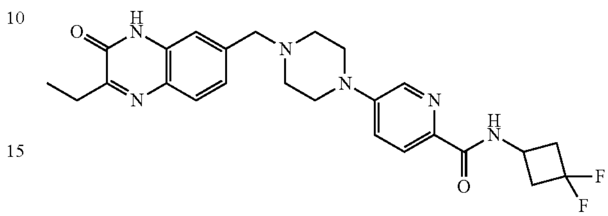
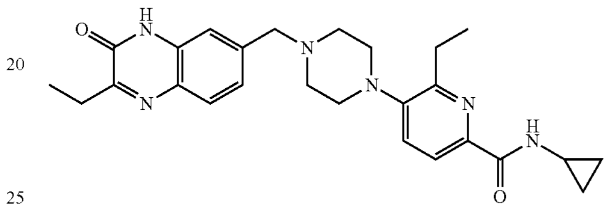
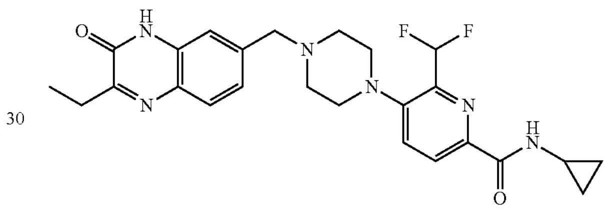
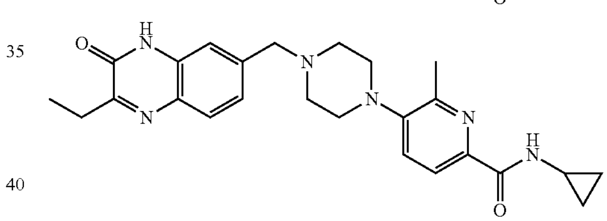
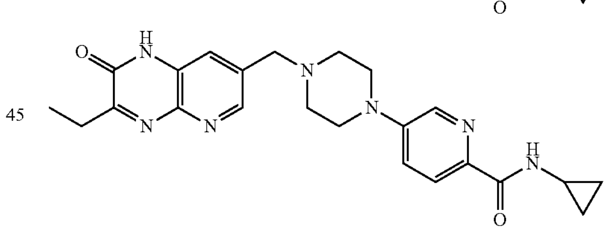
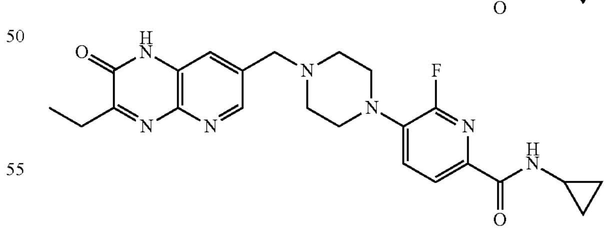
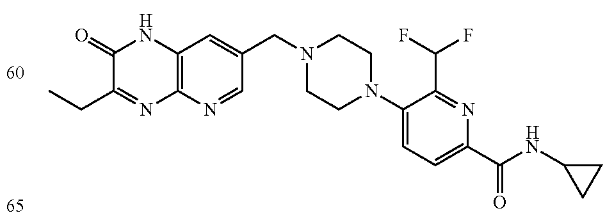

-continued

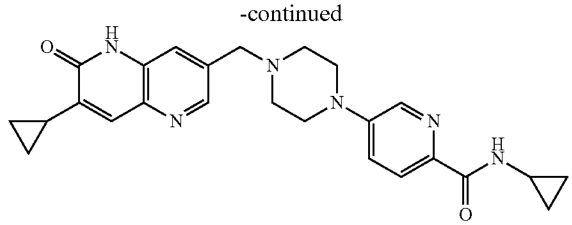

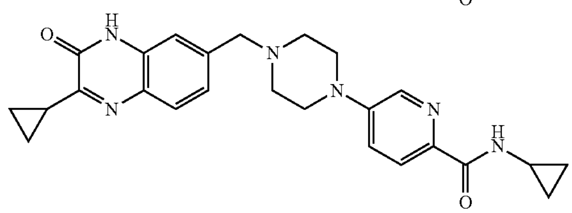

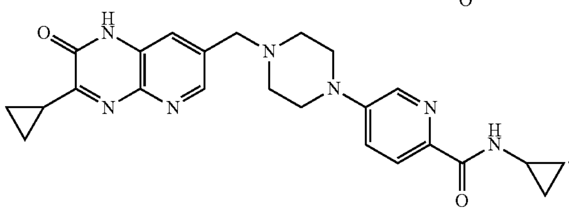

3. A compound of general formula (5), or an optical isomer, a crystalline form, a pharmaceutically acceptable salt, a hydrate, or a solvate thereof:

(5)

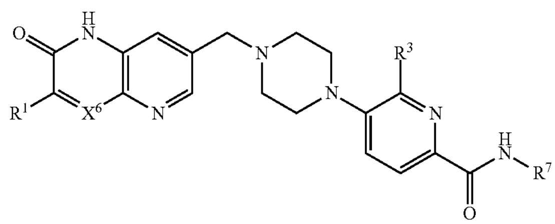

wherein in general formula (5):

$R^1$ is (C1-C4) alkyl, (C1-C4) fluoroalkyl, or (C3-C5) cycloalkyl;

$R^3$ is H, F, Cl, (C1-C4) alkyl, or (C1-C4) fluoroalkyl;

$R^7$ is H, (C1-C4) alkyl or (C3-C4) cycloalkyl substituted with 0-2 F; and $X^6$ is $NR^8$, O or $CR^9R^{10}$, $R^8$ is H or (C1-C3) alkyl, and $R^9$ and $R^{10}$ are each independently H, (C1-C3) alkyl, (C1-C3) fluoroalkyl, or (C3-C4) cycloalkyl.

4. The compound, or the optical isomer, the crystalline form, the pharmaceutically acceptable salt, the hydrate, or the solvate thereof according to claim 3, wherein the compound has one of the following structures:

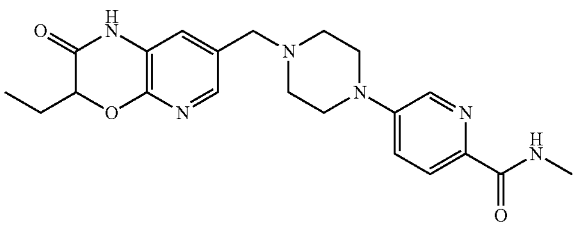

-continued

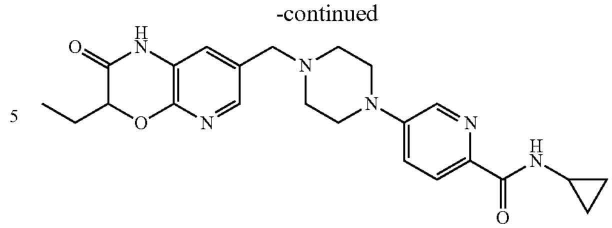

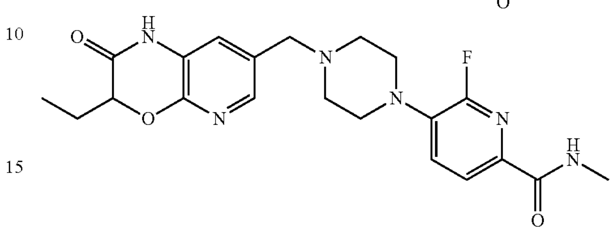

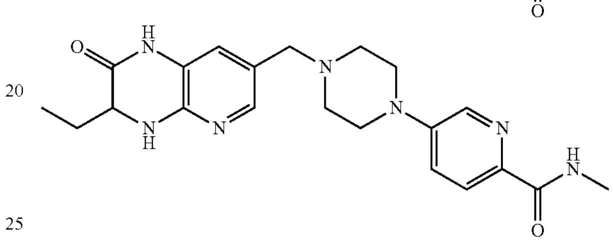

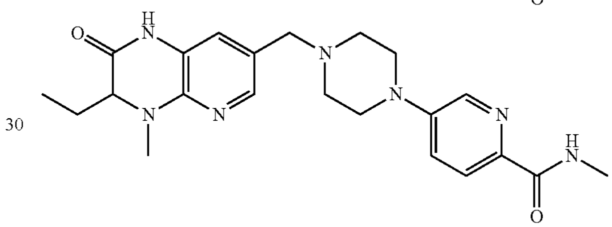

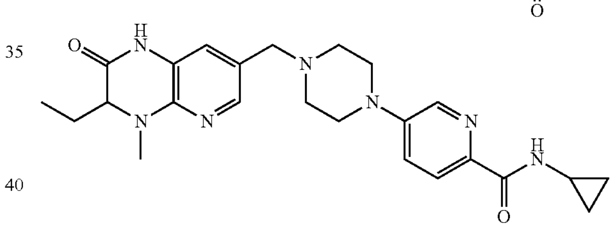

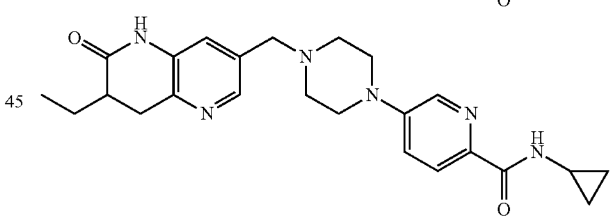

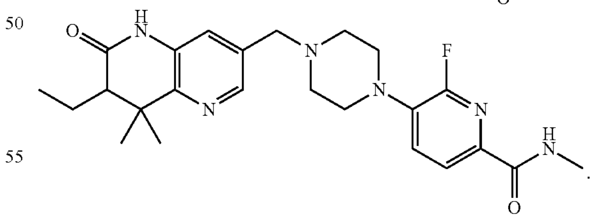

5. A pharmaceutical composition, comprising a pharmaceutically acceptable excipient or carrier, and the compound, or the optical isomer, the crystalline form, the pharmaceutically acceptable salt, the hydrate or the solvate thereof according to claim 1 as an active ingredient.

6. A pharmaceutical composition, comprising a pharmaceutically acceptable excipient or carrier, and the compound, or the optical isomer, the crystalline form, the pharmaceutically acceptable salt, the hydrate or the solvate thereof according to claim 3 as an active ingredient.

* * * * *